United States Patent [19]

Sundelin et al.

[11] Patent Number: 5,716,789
[45] Date of Patent: Feb. 10, 1998

[54] METHOD TO DETERMINE LIGANDS, AGONIST AND ANTAGONIST OF C140 RECEPTOR

[75] Inventors: Johan Sundelin, Furulund, Sweden; Robert M. Scarborough, Belmont, Calif.

[73] Assignee: COR Therapeutics, Inc., San Francisco, Calif.

[21] Appl. No.: 476,000

[22] Filed: Jun. 7, 1995

Related U.S. Application Data

[60] Division of Ser. No. 390,301, Jan. 25, 1995, which is a continuation-in-part of Ser. No. 97,938, Jul. 26, 1993, Pat. No. 5,629,174.

[51] Int. Cl.$^6$ ................................................. G01N 33/566
[52] U.S. Cl. ..................... 435/7.2; 435/7.21; 435/69.1
[58] Field of Search ................................ 435/7.2, 69.1, 435/240.2, 7.21, 252.3, 325

[56] References Cited

U.S. PATENT DOCUMENTS 5,128,254  7/1992  Sibley et al. ........................ 435/172.3

OTHER PUBLICATIONS

R. J. Kaufman, *Methods in Enzymology*, vol. 185, pp. 487–511 (1990): "Vectors Used for Expression in Mammalian Cells".

Masu et al., *Nature*, vol. 329, pp. 836–838 (1987): "cDNA Cloning of Bovine Substance-K Receptor Through Oocyte Expression System".

Scarborough et al., *The Journal of Biological Chemistry*, vol. 267 (19):13146-49 (1982): "Tethered Ligand Agonist Peptides".

VU et al., *Cell*, vol. 64, pp. 1057–1068 (1991): "Molecular Cloning of a Functional Thrombin Receptor Reveals a Novel Proteolytic Mechanism of Receptor Activation".

Patel et al. "Mini Review: The Somatostatin Receptor Family," *Life Sciences* 5(13) 11 Jul. 1995:1249–1265.

Horuk, "Molecular properties of the chemokine receptor family," *TiPS* May 1994, 151(5):159–165.

*Primary Examiner*—John Ulm
*Assistant Examiner*—Karen E. Brown
*Attorney, Agent, or Firm*—Morgan, Lewis & Bockius LLP

[57] ABSTRACT

Nucleic acid molecules encoding the C140 cell surface receptor have been cloned and sequenced. The availability of C140 receptor DNA permits the recombinant production of the C140 receptor which can be produced on the surface of a cell, including an oocyte. The nucleic acid molecules are useful in an assay for detecting a substance which affects C140 receptor activity, either receptor agonists or antagonists. Further, the elucidation of the structure of the C140 receptor permits the design of agonist and antagonist compounds which are useful in such assays. The availability of the C140 receptor also permits production of antibodies specifically immunoreactive with one or more antigenic epitopes of the C140 receptor.

16 Claims, 16 Drawing Sheets

```
                CCCTGTCAGTCTTAAGATTCTAGAAGTCGCTGTCCTATACGGAACCCAAAA
    CTCTCACTGTTAATGAAATACCATTGTCGGGGCGAAGATGTAGCTCAGTGGTAAAATACT -121
    TGCCAGCACACACAAGAATTAGACTTCAACCGTCACCAACTGCCCTGTGTAGGACGGTCG
    GTCACTGAAAGAGAATATTGTCTGCAATACTCTAATGACATCTGTCTGTGTTCATCTGAA -1
                                             SP
    ─────────────────────────────────────────────────────────────
  1 MetPheHisLeuLysHisSerSerLeuThrValGlyProPheIleSerValMetIleLeu
    ATGTTCCATTTAAAACACAGCAGCCTTACTGTTGGACCATTTATCTCAGTAATGATTCTG

─────────────────────────── ▼            ▽
    LeuArgPheLeuCysThrGlyArgAsnAsnSerLysGlyArgSerLeuIleGlyArgLeu
    CTCCGCTTTCTTTGTACAGGACGCAACAACAGTAAAGGAAGAAGTCTTATTGGCAGATTA 120

41 GluThrGlnProProIleThrGlyLysGlyValProValGluProGlyPheSerIleAsp
    GAAACCCAGCCTCCAATCACTGGGAAAGGGGTTCCGGTAGAACCAGGCTTTTCCATCGAT

GluPheSerAlaSerIleLeuThrGlyLysLeuThrThrValPheLeuProValValTyr
    GAGTTCTCTGCGTCCATCCTCACCGGGAAGCTGACCACGGTCTTTCTTCCGGTCGTCTAC 240
                                           I
    ─────────────────────────────────────────────
 81 IleIleValPheValIleGlyLeuProSerAsnGlyMetAlaLeuTrpIlePheLeuPhe
    ATTATTGTGTTTGTGATTGGTTTGCCCAGTAATGGCATGGCCCTCTGGATCTTCCTTTTC
                                           II
                                  ──────────────────────────────
    ArgThrLysLysLysHisProAlaValIleTyrMetAlaAsnLeuAlaLeuAlaAspLeu
    CGAACGAAGAAGAAACACCCCGCCGTGATTTACATGGCCAACCTGGCCTTGGCCGACCTC 360

─────────────
121 LeuSerValIleTrpPheProLeuLysIleSerTyrHisLeuHisGlyAsnAsnTrpVal
    CTCTCTGTCATCTGGTTCCCCCTGAAGATCTCCTACCACCTACATGGCAACAACTGGGTC
                                    III
                      ───────────────────────────────────────
    TyrGlyGluAlaLeuCysLysValLeuIleGlyPhePheTyrGlyAsnMetTyrCysSer
    TACGGGGAGGCCCTGTGCAAGGTGCTCATTGGCTTTTTCTATGGTAACATGTATTGCTCC 480

───────────
161 IleLeuPheMetThrCysLeuSerValGlnArgTyrTrpValIleValAsnProMetGly
    ATCCTCTTCATGACCTGCCTCAGCGTGCAGAGGTACTGGGTGATCGTGAACCCCATGGGA
                                         IV
                              ─────────────────────────────────
    HisProArgLysLysAlaAsnIleAlaValGlyValSerLeuAlaIleTrpLeuLeuIle
    CACCCCAGGAAGAAGGCAAACATCGCCGTTGGCGTCTCCTTGGCAATCTGGCTCCTGATT 600
```

FIG. IA

```
201 PheLeuValThrIleProLeuTyrValMetLysGlnThrIleTyrIleProAlaLeuAsn
    TTTCTGGTCACCATCCCTTTGTATGTCATGAAGCAGACCATCTACATTCCAGCATTGAAC

IleThrThrCysHisAspValLeuProGluGluValLeuValGlyAsnMetPheAsnTyr
    ATCACCACCTGTCACGATGTGCTGCCTGAGGAGGTATTGGTGGGGGACATGTTCAATTAC  720
                                              V
241 PheLeuSerLeuAlaIleGlyValPheLeuPheProAlaLeuLeuThrAlaSerAlaTyr
    TTCCTCTCACTGGCCATTGGAGTCTTCCTGTTCCCGGCCCTCCTTACTGCATCTGCCTAC

ValLeuMetIleLysThrLeuArgSerSerAlaMetAspGluHisSerGluLysLysArg
    GTGCTCATGATCAAGACGCTCCGCTCTTCTGCTATGGATGAACACTCAGAGAACAAAAGG  840
                                             VI
281 GlnArgAlaIleArgLeuIleIleThrValLeuAlaMetTyrPheIleCysPheAlaPro
    CAGAGGGCTATCCGACTCATCATCACCGTGCTGGCCATGTACTTCATCTGCTTTCGTCCT

SerAsnLeuLeuLeuValValHisTyrPheLeuIleLysThrGlnArgGlnSerHisVal
    AGCAACCTTCTGCTCGTAGTGCATTATTTCCTAATCAAAACCCAGAGGCAGAGCCACGTC  960
                                          VII
321 TyrAlaLeuTyrLeuValAlaLeuCysLeuSerThrLeuAsnSerCysIleAspProPhe
    TACGCCCTCTACCTTGTCGCCCTCTGCCTGTCGACCCTCAACAGCTGCATAGACCCCTTT

ValTyrTyrPheValSerLysAspPheArgAspHisAlaArgAsnAlaLeuLeuCysArg
    GTCTATTACTTTGTCTCAAAAGATTTCAGGGATCACGCCAGAAACGCGCTCCTCTGCCGA  1080

361 SerValArgThrValAsnArgMetGlnIleSerLeuSerSerAsnLysPheSerArgLys
    AGTGTCCGCACTGTGAATCGCATGCAAATCTCGCTCAGCTCCAACAAGTTCTCCAGGAAG
    GATGTCAAGCCTGCTTGATGATGATGATGATGATGGTGTGTGTGTG                1246

SerGlySerTyrSerSerSerSerThrSerValLysThrSerTyr
    TCCGGCTCCTACTCTTCAAGCTCAACCAGTGTTAAAACCTCCTACTGAGCTGTACCTGAG 1200
```

FIG.IB

```
                CGCTCCAGGCCTGGGTGACAGCGAGACCCTGTCTCATAAATTAAAAAATGAATAA
_____SP_____
MetAsnValLeuSerPheGluGlnThrSerValThrAlaGluThrPheIleSerValMet
ATGAATGTACTTTCATTTGAACAAACCAGTGTTACTGCTGAAACATTTATTTCTGTAATG
_____▼_____▽_____
ThrLeuValPheLeuSerCysThrGlyThrAsnArgSerSerLysGlyArgSerLeuIle        -1
ACCCTTGTCTTCCTTTCTTGTACAGGAACCAATAGATCCTCTAAAGGAAGAAGCCTTATT      120

GlyLysValAspGlyThrSerHisValThrGlyLysGlyValThrValGluThrValPhe
GGTAAGGTTGATGGCACATCCCACGTCACTGGAAAAGGAGTTACAGTTGAAACAGTCTTT

SerValAspGluPheSerAlaSerValLeuThrGlyLysLeuThrThrValPheLeuPro
TCTGTGGATGAGTTTTCTGCATCTGTCCTCACTGGAAAACTGACCACTGTCTTCCTTCCA      240
_____I_____
IleValTyrThrIleValPheValValGlyLeuProSerAsnGlyMetAlaLeuTrpVal
ATTGTCTACACAATTGTGTTTGTGGTGGGTTTGCCAAGTAACGGCATGGCCCTGTGGGTC

PheLeuPheArgThrLysLysLysHisProAlaValIleTyrMetAlaAsnLeuAlaLeu
TTTCTTTTCCGAACTAAGAAGAAGCACCCTGCTGTGATTTACATGGCCAATCTGGCCTTG      360
_____II_____
AlaAspLeuLeuSerValIleTrpPheProLeuLysIleAlaTyrHisIleHisGlyAsn
GCTGACCTCCTCTCTGTCATCTGGTTCCCCTTGAAGATTGCCTATCACATACATGGCAAC

AsnTrpIleTyrGlyGluAlaLeuCysAsnValLeuIleGlyPhePheTyrGlyAsnMet
AACTGGATTTATGGGGAAGCTCTTTGTAATGTGCTTATTGGCTTTTTCTATGGCAACATG      480
_____III_____
TyrCysSerIleLeuPheMetThrCysLeuSerValGlnArgTyrTrpValIleValAsn
TACTGTTCCATTCTCTTCATGACCTGCCTCAGTGTGCAGAGGTATTGGGTCATCGTGAAC

ProMetGlyHisSerArgLysLysAlaAsnIleAlaIleGlyIleSerLeuAlaIleTrp
CCCATGGGGCACTCCAGGAAGAAGGCAAACATTGCCATTGGCATCTCCCTGGCAATATGG      600
```

FIG. 2A

```
               IV
LeuLeuIleLeuLeuValThrIleProLeuTyrValValLysGlnThrIlePheIlePro
CTGCTGATTCTGCTGGTCACCATCCCTTTGTATGTCGTGAAGCAGACCATCTTCATTCCT
          ▼
AlaLeuAsnIleThrThrCysHisAspValLeuProGluGlnLeuLeuValGlyAspMet     720
GCCCTGAACATCACGACCTGTCATGATGTTTTGCCTGAGCAGCTCTTGGTGGGAGACATG
                                           V
PheAsnTyrPheLeuSerLeuAlaIleGlyValPheLeuPheProAlaPheLeuThrAla
TTCAATTACTTCCTCTCTCTGGCCATTGGGGTCTTTCTGTTCCCAGCCTTCCTCACAGCC

SerAlaTyrValLeuMetIleArgMetLeuArgSerSerAlaMetAspGluAsnSerGlu     840
TCTGCCTATGTGCTGATGATCAGAATGCTGCGATCTTCTGCCATGGATGAAAACTCAGAG
                                      VI
LysLysArgLysArgAlaIleLysLeuIleValThrValLeuAlaMetTyrLeuIleCys
AAGAAAAGGAAGAGGGCCATCAAACTCATTGTCACTGTCCTGGCCATGTACCTGATCTGC

PheThrProSerAsnLeuLeuLeuValValHisTyrPheLeuIleLysSerGlnGlyGln     960
TTCACTCCTAGTAACCTTCTGCTTGTGGTGCATTATTTTCTGATTAAGAGCCAGGGCCAG
                                 VII
SerHisValTyrAlaLeuTyrIleValAlaLeuCysLeuSerThrLeuAsnSerCysIle
AGCCATGTCTATGCCCTGTACATTGTAGCCCTCTGCCTCTCTACCCTTAACAGCTGCATC

AspProPheValTyrTyrPheValSerHisAspPheArgAspHisAlaLysAsnAlaLeu
GACCCCTTTGTCTATTACTTTGTTTCACATGATTTCAGGGATCATGCAAAGAACGCTCTC     1080

LeuCysArgSerValArgThrValLysGlnMetGlnValSerLeuThrSerLysLysHis
CTTTGCCGAAGTGTCCGCACTGTAAAGCAGATGCAAGTATCCCTCACCTCAAAGAAACAC

SerArgLysSerSerSerTyrSerSerSerSerThrThrValLysThrSerTyr *
TCCAGGAAATCCAGCTCTTACTCTTCAAGTTCAACCACTGTTAAGACCTCCTATTGAGTT     1200
```

FIG. 2B

```
Mouse C140  M--FHLKHSS LIVGPFISVM ILLRFLCTGR NNSHKGRSLI GRLETQPPIT  47
Human C140  MNVLSFEQTS VTAETFISVM ILVFLSCTGT NRSSKGRSLI GKVDGTSHVT  50

Mouse C140  GKGVFVEPGF SIDEFSASIL TCKLTTVFLP VVYIIVFVIG LPSNGMALWI  97
Human C140  GKGVIVEIVF SMDEFSASML TGKLTTVFLP IVYIIVFVMG LPSNGMALWV 100

Mouse C140  FLFRTKKKHP AVIYMANLAL ADLLSVIWFP LKISYHLHGN NWMYGEALCK 147
Human C140  FLFRTKKKHP AVIYMANLAL ADLLSVIWFP LKIAYHIHGN NWIYGEALCN 150

Mouse C140  VLIGFFYGNM YCSILFMTCL SVQRYWVIVN PMGHPRKKAN IAMGMSLAIW 197
Human C140  VLIGFFYGNM YCSILFMTCL SVQRYWVIVN PMGHSRKKAN IAIGISLAIW 200

Mouse C140  LLIFLVTIPL YVMKQTIYIP ALNITTCHDV LPEEVLVGDM FNYFLSLAIG 247
Human C140  LLILLVTIPL YVMKQTIPIP ALNITTCHDV LPEQLLVGDM FNYFLSLAIG 250

Mouse C140  VFLFPALLTA SAYVLMIKTL RSSAMDEHSE KKRQRAIRLI ITVLAMYFIC 297
Human C140  VFLFPAFLTA SAYVLMIRML RSSAMDENSE KKRKRAIKLI MTVLAMYLIC 300

Mouse C140  FAPSNLLLVV HYFLIKIQRQ SHVYALYLVA LCLSTLNSCI DPFVYYFVSK 347
Human C140  FIPSNLLLVV HYFLIKSQGQ SHVYALYIVA LCLSTLNSCI DPFVYYFVSH 350

Mouse C140  DFRDHARNAL LCRSVRTVNR MQISLSSNKF SRKSGSYSSS STSVKTSY   395
Human C140  DFRDHAKNAL LCRSVRTVKQ MQMSLISKKH SRKSSSYSSS STTVKTSY   398
```

FIG.3

```
              SP
C140                                                                                              44
HSTHRR  MFHLKHSSLTVGPFISVMILLRFLCTGRNNSK------GRSLIGRLETQP--------                                 60
        MGPRRLLLVAACFSLCGPLLSARTRARRPESKATNATLDPRSFLLRNPNDKYEPEWEDEE
                                                                I
C140    -------PITGKGVPVEPGFSIDEFSASILTGKLTTVFLPVVYIIVFVIGLPSN                                     91
HSTHRR  KNESGLTEYRLVSINKSSPLQKQLPAFISEDASGYLTSSWLTLFVPSYYTGVFVVSLPLN                               120
                                              II
C140    GMALWIFLFRTKKKHPAVIYMANLALADLLSVIWFPLKISYHLHGNNWVYGEALCKVLIG                                151
HSTHRR  IMAIVVFILKMKVKKPAVVYMLHLATADVLFVSVLPFKISYYFSGSDWQFGSELCRFVTA                                180
                III                                            IV
C140    FFYGNMYCSILFMTCLSVQRYWVIVNPM-GHPRKKANIAVGVSLAIWLLIFLVTIPLYVM                                210
HSTHRR  AFYCNMYASILLMTVISIDRFLAVVYPMQSLSWRTLGRASFTCLAIWALAIAGVVPLVLK                                240
                                                     V
C140    KQTIYIPALNITTCHDVLPEEVLVGDMFNYFLSLAIGVFLFPALLTASAYVLMIKTLRSS                                270
HSTHRR  EQTIQVPGLNITTCHDVLNETLLEGYYAYYFSAFSAVFFFVPLIISTVCYVSIIRCLSSS                                300
                                                VI
C140    AMDEHSEKKRQRAIRLIITVLAMYFICFAPSNLLLVVHY-FLIKTQRQSHVYALYLVALC                                329
HSTHRR  AVANRSKKSR--ALFLSAAVFCIFIICFGPTNVLIAHYSFLSHTSTTEAAYFAYLLCVC                                 358
                          VII
C140    LSTLNSCIDPFVYYFVSKDFRDHARNALLCRSVRTVNRMQISLSSNKFSRKSGSYSSSST                                389
HSTHRR  VSSISSCIDPLIYYASSECQRYVYSILCCKESSDPSSYNSSGQLMASKMDTCSSNLNNS                                 418

C140    SVKTSY-                                                                                    395
HSTHRR  IYKKLLT                                                                                    426
```

```
CCCTGTGCTCAGAGTAGGGCTCCGAGTTTCGAACCACTGGTGGCGGATTGCCCGCCCGCC
CCACGTCCGGGGATGCGAAGTCTCAGCCTGGCGTGGCTGCTGGGAGGTATCACCCTTCTG
              M  R  S  L  S  L  A  W  L  L  G  G  I  T  L  L
GCGGCCTCGGTCTCCTGCAGCCGGACCGAGAACCTTGCACCGGGACGCAACAACAGTAAA
 A  A  S  V  S  C  S  R  T  E  N  L  A  P  G  R  N  N  S  K
GGAAGAAGTCTTATTGGCAGATTAGAAACCCAGCCTCCAATCACTGGGAAGGGGTTCCG
 G  R  S  L  I  G  R  L  E  T  Q  P  P  I  T  G  K  G  V  P
GTAGAACCAGGCTTTTCCATCGATGAGTTCTCTGCGTCCATCCTCACCGGGAAGCTGACC
 V  E  P  G  F  S  I  D  E  F  S  A  S  I  L  T  G  K  L  T
ACGGTCTTTCTTCCGGTCGTCTACATTATTGTGTTTGTGATTGGTTTGCCCAGTAATGGC
 T  V  F  L  P  V  V  Y  I  I  V  F  V  I  G  L  P  S  N  G
ATGGCCCTCTGGATCTTCCTTTTCCGAACGAAGAAGAAACACCCCGCCGTGATTTACATG
 M  A  L  W  I  F  L  F  R  T  K  K  K  H  P  A  V  I  Y  M
GCCAACCTGGCCTTGGCCGACCTCCTCTCTGTCATCTGGTTCCCCCTGAAGATCTCCTAC
 A  N  L  A  L  A  D  L  L  S  V  I  W  F  P  L  K  I  S  Y
CACCTACATGGCAACAACTGGGTCTACGGGGAGGCCCTGTGCAAGGTGCTCATTGGCTTT
 H  L  H  G  N  N  W  V  Y  G  E  A  L  C  K  V  L  I  G  F
TTCTATGGTAACATGTATTGCTCCATCCTCTTCATGACCTGCCTCAGCGTGCAGAGGTAC
 F  Y  G  N  M  Y  C  S  I  L  F  M  T  C  L  S  V  Q  R  Y
TGGGTGATCGTGAACCCCATGGGACACCCCAGGAAGAAGGCAAACATCGCCGTTGGCGTC
 W  V  I  V  N  P  M  G  H  P  R  K  K  A  N  I  A  V  G  V
TCCTTGGCAATCTGGCTCCTGATTTTTCTGGTCACCATCCCTTTGTATGTCATGAAGCAG
 S  L  A  I  W  L  L  I  F  L  V  T  P  I  L  Y  V  M  K  Q
ACCATCTACATTCCAGCATTGAACATCACCACCTGTCACGATGTGCTGCCTGAGGAGGTA
 T  I  Y  I  P  A  L  N  I  T  T  C  H  D  V  L  P  E  E  V
TTGGTGGGGGACATGTTCAATTACTTCCTCTCACTGGCCATTGGAGTCTTCCTGTTCCCG
 L  V  G  D  M  F  N  Y  F  L  S  L  A  I  G  V  F  L  F  P
GCCCTCCTTACTGCATCTGCCTACGTGCTCATGATCAAGACGCTCCGCTCTTCTGCTATG
 A  L  L  T  A  S  A  Y  V  L  M  I  K  T  L  R  S  S  A  M
GATGAACACTCAGAGAAGAAAAGGCAGAGGGCTATCCGACTCATCATCACCGTGCTGGCC
 D  E  H  S  E  K  K  R  Q  R  A  I  R  L  I  I  T  V  L  A
ATGTACTTCATCTGCTTTGCTCCTAGCAACCTTCTGCTCGTAGTGCATTATTTCCTAATC
 M  Y  F  I  C  F  A  P  S  N  L  L  L  V  V  H  Y  F  L  I
AAAACCCAGAGGCAGAGCCACGTCTACGCCCTCTACCTTGTCGCCCTCTGCCTGTCGACC
 K  T  Q  R  Q  S  H  V  Y  A  L  Y  L  V  A  L  C  L  S  T
CTCAACAGCTGCATAGACCCCTTTGTCTATTACTTTGTCTCAAAAGATTTCAGGGATCAC
 L  N  S  C  I  D  P  F  V  Y  Y  F  V  S  K  D  F  R  D  H
```

FIG. 10A

```
GCCAGAAACGCGCTCCTCTGCCGAAGTGTCCGCACTGTGAATCGCATGCAAATCTCGCTC
 A  R  N  A  L  L  C  R  S  V  R  T  V  N  R  M  Q  I  S  L
AGCTCCAACAAGTTCTCCAGGAAGTCCGGCTCCTACTCTTCAAGCTCAACCAGTGTTAAA
 S  S  N  K  F  S  R  K  S  G  S  Y  S  S  S  S  T  S  V  K
ACCTCCTACTGAGCTGTACCTGAGGATGTCAAGCCTGCTTGATGATGATGATGATGATGG
 T  S  Y
TGTGTGTGTGTGTGTGTGTGTGTGTGTGTGTGTGTGTGCACCCGTGTGTGAGTGCGTG
GTAGGGATACACCAACATGGATGGGGCTGTCATTTCCTATCCAAGCTGTCTGTCTCTGCA
CCAATCACAAGCATGCAGCTCTCCCCAGGATTGACAGAAGCCTCCTCCTTTGCATGAGAA
CAGTCTTCCACTCTGATGAAAAGCATCAGTATCAGAAACTGAAACGAACTGAGAGGAGCT
TGTTTTGTGAAAGTGAAGAGAAGATGGAGGGTCAGTGACTTGCAAAAAAAACCAACCAAA
CAAAAACTACACCTGGCAAGAAGGCTAAGACTCTCTGAAATGCTTCCCTTTTCCATCTGG
AGTTCGTCTCGGCCTTGTTCAGGACCTGAGGCCCTGGTAGAGCTTCAGTCCAGTTGATTG
ACTTTACAGACTTGAGAGAGGAGTGAATGAGGAGTGAATGAGGCTCCTGGCGGCATCCTA
ACCGGCTAACAGTGGCCTTGCTGGACAATAGGATTCAGATGGCTGGAGTTACATTCTCAC
ACCATTTCATCAGAACTATTGGGGATCTTGATCAATGTGCAGGTCCCTTAGCGTCAGTAA
CCCTGGGAGCTCAGACACGATGGGGGTGAGGGTGGGGGTGGGGGTGGGGGTGAGGCTCTA
CAAACCTTAGTGATGACTGCAGACACAGAACCATGGAGCTGAGCCTGCTTCTGCTTGCCA
GGGCACCACTGTAATGTTGGCAAAGAAAAACCAACAGCAGTGTTTTGAGCCTCTTTTTTT
GGTCAGTTTATGATGAATTTGCCTATTGGTTTATTGGGATTTTCAGTTCCTTTATTACTT
TGTTGTAATTTTGTGTGTTTATTAGTCAAGAAAAGAAGATGAGGCTCTTAAAAATGTAA
ATAAAATTTTTGGTTTTTTGGTTTTTTAACTTGGGCCAACTACAAATACTGCTTAGGTTT
TTTTCTAACTTAATTGTTAACTACATCATGTGAACTTAAGACATTTTCATGATAAAGCAT
TACTGTAGTGTCAGTTTTCCCTCATCCTCGATCATAGTCCTTCCCGTGAAGCAGGGCCCT
TCCCCTCCCCCCCCTTTGCCGTTTCCCTCCCCACCAGATAGTCCCCCTGTCTGCTTTAAC
CTACCAGTTAGTATTTTATAAAAACAGATCATTGGAATATTTATTATCAGTTTTGTTCAC
TTGTTATCAGTTTTGTTCACTAATTTGTCCAATAATGGAATTAACGTCTTCTCATCTGTT
TGAGGAAGATCTGAAACAAGGGGCCATTGCAGGAGTACATGGCTCCAGGCTTACTTTATA
TACTGCCTGTATTTGTGGCTTTAAAAAAATGACCTTGTTATATGAATGCTTTATAAATAA
ATAATGCATGAACTTTAAAAAAAAAAAAAAAA
```

FIG. 10B

```
          10        20        30        40        50        60
123456789012345678901234567890123456789012345678901234567890
CAAAGAATTGTAATACGACTCACTATAGGGCGAATTCGGATCCAGGAGGATGCGGAGCCC
                                                   MetArgSerPr
```

```
          70        80        90        100       110       120
123456789012345678901234567890123456789012345678901234567890
CAGCGCGGCGTGGCTGCTGGGGGCCGCCATCCTGCTAGCAGCCTCTCTCTCCTGCAGTGG   120
oSerAlaAlaTrpLeuLeuGlyAlaAlaIleLeuLeuAlaAlaSerLeuSerCysSerGl
```

```
CACCATCCAAGGAACCAATAGATCCTCTAAAGGAAGAAGCCTTATTGGTAAGGTTGATGG
yThrIleGlnGlyThrAsnArgSerSerLysGlyArgSerLeuIleGlyLysValAspGl

CACATCCCACGTCACTGGAAAAGGAGTTACAGTTGAAACAGTCTTTTCTGTGGATGAGTT   240
yThrSerHisValThrGlyLysGlyValThrValGluThrValPheSerValAspGluPh

TTCTGCATCTGTCCTCGCTGGAAAACTGACCACTGTCTTCCTTCCAATTGTCTACACAAT
eSerAlaSerValLeuAlaGlyLysLeuThrThrValPheLeuProIleValTyrThrIl

TGTGTTTGCGGTGGGTTTGCCAAGTAACGGCATGGCCCTATGGGTCTTTCTTTTCCGAAC   360
eValPheAlaValGlyLeuProSerAsnGlyMetAlaLeuTrpValPheLeuPheArgTh

TAAGAAGAAGCACCCTGCTGTGATTTACATGGCCAATCTGGCCTTGGCTGACCTCCTCTC
rLysLysLysHisProAlaValIleTyrMetAlaAsnLeuAlaLeuAlaAspLeuLeuSe

TGTCATCTGGTTCCCCTTGAAGATTGCCTATCACATACATGGCAACAACTGGATTTATGG   480
rValIleTrpPheProLeuLysIleAlaTyrHisIleHisGlyAsnAsnTrpIleTyrGl

GGAAGCTCTTTGTAATGTGCTTATTGGCTTTTTCTATCGCAACATGTACTGTTCCATTCT
yGluAlaLeuCysAsnValLeuIleGlyPhePheTyrArgAsnMetTyrCysSerIleLu

CTTCATGACCTGCCTCAGTGTGCAGAGGTATTGGGTCATCGTGAACCCCATGGGGCACTC   600
uPheMetThrCysLeuSerValGlnArgTyrTrpValIleValAsnProMetGlyHisSe

CAGGAAGAAGGCAAACATTGCCATTGGCATCTCCCTGGCAATATGGCTGCTGACTCTGCT
rArgLysLysAlaAsnIleAlaIleGlyIleSerLeuAlaIleTrpLeuLeuThrLeuLe

GGTCACCATCCCTTTGTATGTCGTGAAGCAGACCATCTTCATTCCTGCCCTGAACATCAC   720
uValThrIleProLeuTyrValValLysGlnThrIlePheIleProAlaLeuAsnIleTh
```

FIG. 11A

```
GACCTGTCATGATGTTTTGCCTGAGCAGCTCTTGGTGGGAGACATGTTCAATTACTTCCT
rThrCysHisAspValLeuProGluGlnLeuLeuValGlyAspMetPheAsnTyrPheLe

CTCTCTGGCCATTGGGGTCTTTCTGTTCCCAGCCTTCCTCACAGCCTCTGCCTATGTGCT      840
uSerLeuAlaIleGlyValPheLeuPheProAlaPheLeuThrAlaSerAlaTyrValLe

GATGATCAGAATGCTGCGATCTTCTGCCATGGATGAAAACTCAGAGAAGAAAAGGAAGAG
uMetIleArgMetLeuArgSerSerAlaMetAspGluAsnSerGluLysLysArgLysAr

GGCCATCAAACTCATTGTCACTGTCCTGGGCATGTACCTGATCTGCTTCACTCCTAGTAA      960
gAlaIleLysLeuIleValThrValLeuGlyMetTyrLeuIleCysPheThrProSerAs

CCTTCTGCTTGTGGTGCATTATTTTCTGATTAAGAGCCAGGGCCAGAGCCATGTCTATGC
nLeuLeuLeuValValHisTyrPheLeuIleLysSerGlnGlyGlnSerHisValTyrAl

CCTGTACATTGTAGCCCTCTGCCTCTCTACCCTTAACAGCTGCATCGACCCCTTTGTCTA     1080
aLeuTyrIleValAlaLeuCysLeuSerThrLeuAsnSerCysIleAspProPheValTy

TTACTTTGTTTCACATGATTTCAGGGATCATGCAAAGAACGCTCTCCTTTGCCGAAGTGT
rTyrPheValSerHisAspPheArgAspHisAlaLysAsnAlaLeuLeuCysArgSerVa

CCGCACTGTAAAGCAGATGCAAGTACCCCTCACCTCAAAGAAACACTCCAGGAAATCCAG     1200
lArgThrValLysGlnMetGlnValProLeuThrSerLysLysHisSerArgLysSerSe

CTCTTACTCTTCAAGTTCAACCACTGTTAAGACCTCCTATTGAGTTTTCCAGGTCCTCAG
rSerTyrSerSerSerSerThrThrValLysThrSerTyr

ATGGGAATTGCACAGTAGGATGTGGAACCTGTTTAATGTTATGAGGACGTGTCTGTTATT     1320

TCCGGATCCAGATCTTATTAAAGCAGAACTTGTTTATTGCAGCTTATAATGGTTACAAAT

AAAGCAATAGCATCACAAATTTCACAAATAAAGC                                1414
```

METHOD TO DETERMINE LIGANDS, AGONIST AND ANTAGONIST OF C140 RECEPTOR

This application is a division of application Ser. No. 08/390,301 filed 25 Jan., 1995, which is a continuation-in-part of application Ser. No. 08/097,938 filed 26 Jul., 1993 now U.S. Pat. No. 5,629,174.

TECHNICAL FIELD

The invention relates to a newly discovered receptor which is a member of the G-protein-coupled receptor superfamily. The receptor is expressed in endothelial cells in blood vessels. Avoidance of effects on this receptor is an essential element in limiting side effects of drugs which are administered to stimulate other receptors in this family. The invention also relates to nucleic acid sequences encoding the receptor protein or peptide.

BACKGROUND ART

Responses of animals to many therapeutic and prophylactic drugs are mediated through receptors which reside on cell surfaces. One class of such receptors comprises the G-protein-coupled receptors, whose physiological effect is mediated by a three-subunit protein complex, called G-proteins, that binds to this type of receptor with the subsequent release of a subunit, thus setting in motion additional intracellular events. Receptors of this subclass include, among others, adrenergic receptors, neuropeptide receptors, the thrombin receptor and the C140 receptor which is the subject of the herein invention. This class of receptor is characterized by the presence of seven transmembrane regions which anchor the receptor within the cell surface.

It is the elusive goal of the designers of therapeutic substances to effect a desired response in a subject in the absence of side effects. Accordingly, pharmaceuticals designed to target a specific receptor, such as the thrombin receptor, should react with the thrombin receptor specifically and have no effect on related receptors. The C140 receptor of the present invention may be involved in controlling vascular pressure, and inadvertent stimulation or blocking of this receptor would have unpredictable and therefore undesirable results. It is therefore useful to determine in advance whether therapeutic reagents designed to target, for example, the thrombin receptor will or will not have the undesired side effect of reactivity with the C140 receptor. By providing the recombinant materials for the production of the C140 receptor in convenient assay systems, as well as agonist and antagonist reagents for use in this assay, the invention makes possible the prior determination of the presence or absence of the side effect of reactivity with the C140 receptor in candidate pharmaceuticals. This side effect will usually be undesired as it is believed that the C140 receptor responds to enzymes such as serine proteases associated with trauma and immune disturbances.

DISCLOSURE OF THE INVENTION

The invention provides methods and materials useful in assay systems to determine the propensity of candidate pharmaceuticals to exert undesirable side effects. The isolation, recombinant production and characterization of the C140 receptor permits the design of assay systems using the receptor as a substrate and using agonists and antagonists for the receptor as control reagents in the assay.

Thus, in one aspect, the invention is directed to recombinant materials associated with the production of C140

2 receptor. These include, for example, transfected cells which can be cultured so as to display the C140 receptor on their surfaces, and thus provide an assay system for the interaction of materials with the native C140 receptor. In general, the limitations on the host cells useful in these assay systems are that the cells have the appropriate mechanism to display the receptor on their surfaces and contain the G-protein as mediator to the intracellular response. (However assays which merely assess binding do not require the G-protein.) Most animal cells meet these requirements.

In another aspect, the invention is directed to C140 receptor agonists which mimic the activated form of the extracellular portion of the receptor protein. These agonists are useful as control reagents in the above-mentioned assays to verify the workability of the assay system. In addition, agonists for the C140 receptor may exhibit hypotensive effects in vivo. Accordingly, the agonists may be also, themselves, useful as antihypertensives.

In still another aspect, the invention is directed to C140 receptor antagonists. These antagonists comprise modified forms of the C140 receptor agonist peptides that lack the essential features required for activation of the receptor. These antagonists bind to receptor, do not activate it, and prevent receptor activation by agonists and the native receptor-binding ligand.

A second group of antagonists includes antibodies designed to bind specific portions of the receptor protein. In general, these are monoclonal antibody preparations which are highly specific for any desired region of the C140 receptor. The antibodies of the invention are also useful in immunoassays for the receptor protein, for example, in assessing successful expression of the gene in recombinant systems.

Another aspect of the invention is to provide nucleic acids encoding such a C140 receptor polypeptide and to use this nucleic acid to produce the polypeptide in recombinant cell culture for diagnostic use or for potential therapeutic use in hemostatic or immune response regulation.

In still other aspects, the invention provides an isolated nucleic acid molecule encoding a C140 receptor, labeled or unlabeled, and a nucleic acid sequence that is complementary to, or hybridizes under stringent conditions to, a nucleic acid sequence encoding a C140 receptor. The isolated nucleic acid molecule of the present invention excludes nucleic acid sequences which encode, or are complementary to nucleic acid sequences encoding, other known G protein-coupled receptors which are not C140 receptors, such as adrenergic receptors, neuropeptide receptors, thrombin receptors, and the like.

In addition, the invention provides a replicable vector comprising a nucleic acid molecule encoding a C140 receptor operably linked to control sequences recognized by a host transformed by the vector; host cells transformed with the vector; and a method of using a nucleic acid molecule encoding a C140 receptor to effect the production of a C140 receptor, comprising expressing the nucleic acid molecule in a culture of the transformed host cells and recovering a C140 receptor from the host cell culture. The nucleic acid sequence is also useful in hybridization assays for C140 receptor-encoding nucleic acid molecules.

In still further embodiments, the invention provides a method for producing C140 receptors comprising inserting into the DNA of a cell containing the nucleic acid sequence encoding a C140 receptor a transcription modulatory element in sufficient proximity and orientation to the C140 receptor coding sequence to influence transcription thereof, with an optional further step comprising culturing the cell containing the transcription modulatory element and the C140 receptor-encoding nucleic acid sequence.

In still further embodiments, the invention provides a cell comprising a nucleic acid sequence encoding a C140 receptor and an exogenous transcription modulatory element in sufficient proximity and orientation to the above coding sequence to influence transcription thereof; and a host cell containing the nucleic acid sequence encoding a C140 receptor operably linked to exogenous control sequences recognized by the host cell.

Still further is provided a method for obtaining cells having increased or decreased transcription of the nucleic acid molecule encoding a C140 receptor, comprising:

(a) providing cells containing the nucleic acid molecule;

(b) introducing into the cells a transcription modulating element; and (c) screening the cells for a cell in which the transcription of the nucleic acid molecule is increased or decreased.

In another aspect, the invention is related to assay systems which utilize recombinant C140 receptor to screen for agonist and antagonist activity of candidate drugs. This assay is especially useful in assuring that these therapeutic agents do not have undesired side effects caused by activation or inhibition of the C140 receptor. In some cases agonist activity at this receptor system may have therapeutic utility. Some of these assay systems include the use of the agonist peptides as positive controls. The assay can also be used to screen for antagonists which inhibit the agonistic effect.

Another aspect of the invention relates to the diagnosis of conditions characterized by activation of the C140 receptor by detection in fluids, such as blood or urine, of the peptide cleaved from the C140 receptor when the receptor is activated. Another diagnostic method included in the invention is visualization of the activated forms of receptor by localizing an imaging agent to activated receptor in situ using antibodies specific to the activated receptor.

Yet another aspect of this invention relates to the therapeutic, prophylactic and research uses of various techniques to block or modulate the expression of a C140 receptor by interfering with the transcription of translation of a DNA or RNA molecule encoding the C140 receptor. This includes a method to inhibit or regulate expression of C140 receptors in a cell comprising providing to the cell an oligonucleotide molecule which is antisense to, or forms a triple helix with, C140 receptor-encoding DNA or with DNA regulating expression of C140 receptor-encoding DNA, in an amount sufficient to inhibit or regulate expression of the C140 receptors, thereby inhibiting or regulating their expression. Also included is a method to inhibit or regulate expression of C140 receptors in a subject, comprising administering to the subject an oligonucleotide molecule which is antisense to, or forms a triple helix with, C140 receptor-encoding DNA or with DNA regulating expression of C140 receptor-encoding DNA, in an amount sufficient to inhibit or regulate expression of the C140 receptors in the subject, thereby inhibiting or regulating their expression. The antisense molecule or triple helix-forming molecule in the above methods is preferably a DNA or RNA oligonucleotide.

Additional aspects of the invention are directed to pharmaceutical compositions containing the agonists and antagonists of the invention. The agonists of the invention are antihypertensives; conversely, the antagonists can elevate blood pressure if desired. Other aspects of the invention include a pharmaceutical composition useful for inhibiting or regulating C140 receptor expression in a cell or in a subject at the level of transcription or translation, which composition comprises an antisense or triple helix-forming molecule as described above which corresponds to a portion of the sequence of the C140 receptor-coding nucleic acid.

BRIEF DESCRIPTION OF THE DRAWINGS

FIGS. 1A–1B (SEQ ID NO: 1 and SEQ ID NO: 2) show the DNA and deduced amino acid sequence of murine C140 receptor.

FIGS. 2A–2B (SEQ ID NO: 3 and SEQ ID NO: 4) show the DNA and deduced amino acid sequence of human C140 receptor.

FIG. 3 (SEQ ID NO: 5 and SEQ ID NO: 6) shows a comparison of amino acid sequences for the human C140 receptor and murine C140 receptor.

FIG. 5 (SEQ ID NO: 5 and SEQ ID NO: 7) shows a comparison of amino acid sequences for the mouse C140 receptor and the human thrombin receptor.

FIG. 8a shows these results in the immobilized vein; FIG. 8b shows these results for the immobilized vein depleted of endothelial cells.

FIG. 9a shows the results for plasmin; FIG. 9b shows the results for kallikrein; FIG. 9c shows the results for trypsin.

FIGS. 10A–10B (SEQ ID NO: 60 and SEQ ID NO: 61) show the nucleotide sequence and deduced amino acid sequence of a cDNA clone encoding murine C140 receptor.

FIGS. 11A–11B (SEQ ID NO: 62 and SEQ ID NO: 63) show the nucleotide sequence and deduced amino acid sequence of a cDNA clone encoding human C140 receptor.

MODES OF CARRYING OUT THE INVENTION

The characteristics of the C140 receptor elucidated by the invention herein are summarized in FIGS. 1A/1B-4. FIGS. 1A–1B shows the complete DNA sequence of the clone encoding the murine receptor, along with the deduced amino acid sequence. As used herein, the "C140 receptor" refers to receptor in any animal species corresponding to the murine receptor contained in clone C140 described in Example 1 herein. Using the native DNA encoding the murine form of this receptor, the corresponding receptors in other species, including humans, as illustrated herein, may be obtained. FIGS. 2A–2B shows the corresponding DNA and deduced amino acid sequence of the human receptor.

The entire amino acid sequence of the murine receptor contains 395 amino acids, including a 27 amino acid signal peptide which, when cleaved, results in a 368 amino acid mature receptor protein. Similarly, the human receptor is encoded by an open reading frame corresponding to 398 amino acids including a probable 29 amino acid signal peptide sequence resulting in a 369 amino acid mature receptor protein, as shown in FIGS. 2A–2B.

FIG. 3 shows a comparison of the human and murine amino acid sequences; as shown, these sequences exhibit a high degree of homology.

Figure 4:
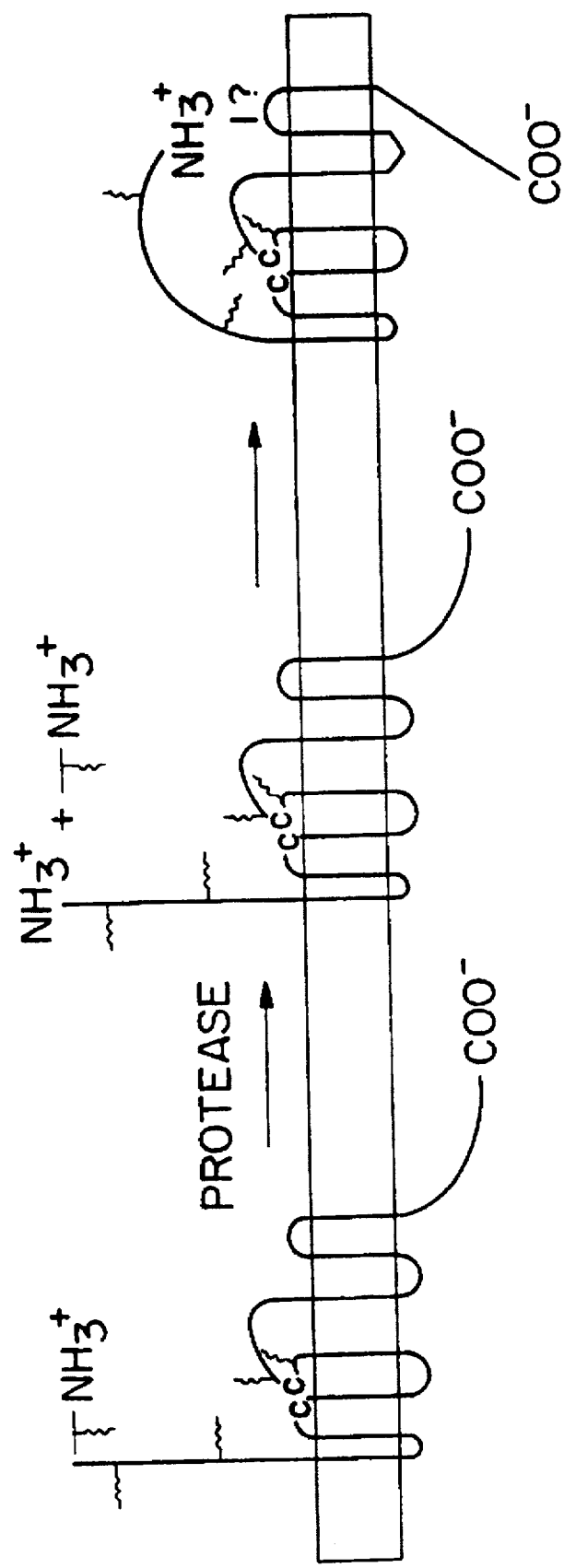
FIG. 4 shows a proposed model of C140 receptor activation based on the deduced amino acid sequence.

Hydrophobicity/hydrophilicity plots of the sequences shown in FIGS. 1A–1B and 2A–2B indicate that the mature C140 receptor is a member of the 7-transmembrane domain receptor family whose effect on the cell is mediated by G-protein. The mature C140 receptor has a relatively long extracellular amino acid extension containing several consensus sites for asparagine-linked glycosylation. It also contains a conserved asparagine in the first transmembrane region, the motif Leu-Ala-X-X-Asp in the second transmembrane region, a Trp in the fourth transmembrane region and a carboxy terminal tail which contains multiple serine and threonine residues. A proposed model of the in situ receptor is shown in FIG. 4.

Referring to FIG. 5, similarities to the thrombin receptor are readily seen. FIG. 5 compares the amino acid sequence of murine C140 with that of thrombin receptor. It is known that the thrombin receptor is activated by proteolytic cleavage of the Arg-Ser bond at positions 41 and 42, which releases an activation peptide that permits refolding of the receptor and activation via the newly created amino terminus. In an analogous manner, the C140 receptor is activated by cleavage of the Arg-Ser bond at positions 34 and 35, also liberating an activation peptide extending from position 1 of the putative mature protein to the cleavage site. It is believed that Arg-28 is the amino terminal amino acid residue of the mature protein, so the activation peptide has the sequence RNNSKGR (SEQ ID NO: 8). This peptide could thus be used as an index for activation of C140 receptor. In any event, the precise location of the N-terminus of the mature protein is unimportant for the design of agonists or antagonists. The activation peptide is likely to be freely filtered by the kidney and possibly concentrated in the urine and can be used as an index to activation of the C140 receptor.

Release of the activation peptide permits refolding of the receptor protein to activate the receptor. This is shown schematically in FIG. 4, which also shows that the conformational changes resulting from the liberation of the activation peptide and refolding results in an intracellular conformational change of the receptor. This hypothesis is confirmed by the finding that the C140 receptor can be activated by a peptide mimicking the new amino terminus created by the activation. Accordingly, mimics of the N-terminus of the new amino terminus on the activated receptor behave as agonists therefor. The importance of the first five amino acids in the newly created amino terminus in the receptor for receptor activation has also been confirmed hereinbelow.

Based on this information, and by analogy with the mechanisms underlying trypsinogen activation to trypsin and activation of the thrombin receptor, it appears that the positively charged amino group on serine that is newly exposed when the ligand cleaves the receptor plays an important role in receptor activation. Peptides based on the agonist peptide sequence that bind the C140 receptor, but which are modified to be lacking the free α-amino group can function as antagonists of this receptor. Thus, modifications of the agonist peptides which lack the capacity for specific activating interaction serve as C140 receptor antagonists.

Ordinarily, the C140 receptors and analogs thereof claimed herein will have an amino acid sequence having at least 75% amino acid sequence identity with a "common" C140 receptor sequence (such as that disclosed in FIGS. 1A–1B or FIGS. 2A–2B), more preferably at least 80%, even more preferably at least 90%, and most preferably at least 95%. Identity or homology with respect to a common sequence is defined herein as the percentage of amino acid residues in the candidate sequence that are identical with the known C140 receptor, after aligning the sequences and introducing gaps, if necessary, to achieve the maximum percent homology, and not considering any conservative substitutions as part of the sequence identity. None of N-terminal, C-terminal or internal extensions, deletions, or insertions into the C140 receptor sequence shall be construed as affecting homology.

Thus, the claimed C140 receptor and analog molecules that are the subject of this invention include molecules having the C140 receptor amino acid sequence; fragments thereof having a consecutive sequence of at least 10, 15, 20, 25, 30 or 40 amino acid residues from a common C140 receptor sequence; amino acid sequence variants of a common C140 receptor sequence wherein an amino acid residue has been inserted N- or C-terminal to, or within, the C140 receptor sequence or its fragments as defined above; amino acid sequence variants of the common C140 receptor sequence or its fragment as defined above which have been substituted by another residue. C140 receptor polypeptides include those containing predetermined mutations by, e.g., homologous recombination, site-directed or PCR mutagenesis, and C140 receptor polypeptides of other animal species, including but not limited to rabbit, rat, murine, porcine, bovine, ovine, equine and non-human primate species, and alleles or other naturally occurring variants of the C140 receptor of the foregoing species and of human sequences; derivatives of the commonly known C140 receptor or its fragments wherein the C140 receptor or its fragments have been covalently modified by substitution, chemical, enzymatic, or other appropriate means with a moiety other than a naturally occurring amino acid (for example a detectable moiety such as an enzyme or radioisotope); glycosylation variants of C140 receptor (insertion of a glycosylation site or deletion of any glycosylation site by deletion, insertion or substitution of appropriate amino acid); and soluble forms of C140.

The novel proteins and peptides of the present invention are preferably those which share a common biological activity with the C140 receptor, including but not limited to an effector or receptor function or cross-reactive antigenicity. Such fragments and variants exclude any C140 receptor polypeptide heretofore made public, including any known protein or polypeptide of any animal species, which is otherwise anticipatory under 35 U.S.C. §102 as well as polypeptides obvious over such known protein or polypeptides under 35 U.S.C. §103. Specifically, the present C140 receptor proteins, analogs, fragments and variants exclude other known G protein-coupled receptors which are not C140 receptors, such as adrenergic receptors, neuropeptide receptors, thrombin receptors, and the like.

COMPOUNDS OF THE INVENTION

The nomenclature used to describe the peptide compounds of the invention follows the conventional practice where the N-terminal amino group is assumed to be to the left and the carboxy group to the right of each amino acid residue in the peptide. In the formulas representing selected specific embodiments of the present invention, the aminoand carboxy-terminal groups, although often not specifically shown, will be understood to be in the form they would assume at physiological pH values, unless otherwise specified. Thus, the N-terminal $H^+_2$ and C-terminal $O^-$ at physiological pH are understood to be present though not necessarily specified and shown, either in specific examples or in generic formulas. Free functional groups on the side chains of the amino acid residues can also be modified by amidation, acylation or other substitution, which can, for example, change the solubility of the compounds without affecting their activity.

In the peptides shown, each gene-encoded residue, where appropriate, is represented by a single letter designation, corresponding to the trivial name of the amino acid, in accordance with the following conventional list:

| Amino Acid | One-Letter Symbol | Three-letter Symbol |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acids not encoded genetically are abbreviated as indicated in the discussion below.

In the specific peptides shown in the present application, the L-form of any amino acid residue having an optical isomer is intended unless the D-form is expressly indicated by a dagger superscript (†).

The compounds of the invention are peptides which are partially defined in terms of amino acid residues of designated classes. Amino acid residues can be generally subclassified into four major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows.
Acidic: Aspartic acid and Glutamic acid;
Basic/noncyclic: Arginine, Lysine;
Basic/cyclic: Histidine;
Neutral/polar/small: Glycine, serine, cysteine;
Neutral/nonpolar/small: Alanine;
Neutral/polar/large/nonaromatic: Threonine, Asparagine, Glutamine;
Neutral/polar/large aromatic: Tyrosine;
Neutral/nonpolar/large/nonaromatic: Valine, Isoleucine, Leucine, Methionine;
Neutral/nonpolar/large/aromatic: Phenylalanine, and Tryptophan The gene-encoded secondary amino acid proline, although technically within the group neutral/nonpolar/large/cyclic and nonaromatic, is a special case due to its known effects on the secondary conformation of peptide chains, and is not, therefore, included in this defined group.

Certain commonly encountered amino acids, which are not encoded by the genetic code, include, for example, beta-alanine (beta-Ala), or other omega-amino acids, such as 3-amino propionic, 2,3-diamino propionic (2,3-diaP), 4-amino butyric and so forth, alpha-aminisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) 2-naphthylalanine (2-Nal); 1,2,3,4-tetrahydroisoquinoline-3-carboxylic acid (Tic); β-2-thienylalanine (Thi); and methionine sulfoxide (MSO). These also fall conveniently into particular categories.

Based on the above definitions,

Sar, beta-Ala, 2,3-diaP and Aib are neutral/nonpolar/small;

t-BuA, t-BuG, N-MeIle, Nle, Mvl and Cha are neutral/nonpolar/large/nonaromatic;

Orn is basic/noncyclic;

Cya is acidic;

Cit, Acetyl Lys, and MSO are neutral/polar/large/nonaromatic; and

Phg, Nal, Thi and Tic are neutral/nonpolar/large/aromatic.

The various omega-amino acids are classified according to size as neutral/nonpolar/small (beta-Ala, i.e., 3-aminopropionic, 4-aminobutyric) or large (all others).

Other amino acid substitutions of those encoded in the gene can also be included in peptide compounds within the scope of the invention and can be classified within this general scheme according to their structure.

All of the compounds of the invention, when an amino acid forms the C-terminus, may be in the form of the pharmaceutically acceptable salts or esters. Salts may be, for example, Na⁺, K⁺, $Ca^{+2}$, $Mg^{+2}$ and the like; the esters are generally those of alcohols of 1–6C.

In all of the peptides of the invention, one or more amide linkages (—CO—NH—) may optionally be replaced with another linkage which is an isostere such as —CH₂NH—, —CH₂S—, —CH₂CH₂, —CH=CH— (cis and trans), —COCH₂—, —CH(OH)CH₂— and —CH₂SO—. This replacement can be made by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 (—CH₂NH—, —CH₂CH₂—); Spatola, A. F., et al., *Life Sci* (1986) 38:1243–1249 (—CH₂—S); Hann, M. M., *J Chem Soc Perkin Trans I* (1982) 307–314 (—CH—CH—, cis and trans); Almquist, R. G., et al., *J Med Chem* (1980) 23:1392–1398 (—COCH₂—); Jennings-White, C., et al., *Tetrahedron Lett* (1982) 23:2533 (—COCH₂—); Szelke, M., et al., European Application EP 45665 (1982) CA:97:39405 (1982) (—CH(OH)CH₂—); Holladay, M. W., et al., *Tetrahedron Lett* (1983) 24:4401–4404 (—C(OH)CH₂—); and Hruby, V. J., *Life Sci* (1982) 31:189–199 (—CH₂—S—).

A. Agonists

The agonists of the invention comprise a series of peptides of the formula

   (1)

wherein AA₁ is a small amino acid or threonine;

AA₂ and AA₃ are each independently neutral/nonpolar/large/nonaromatic amino acids;

AA₄ is a small amino acid;

AA₅ is a basic amino acid;

AA₆ may be present or absent and, if present, is a neutral/nonpolar/large/nonaromatic amino acid;

AA₇ is absent if AA₆ is absent and may be present or absent if AA₆ is present, and is an acidic amino acid; and Z is a substituent that does not interfere with agonist activity.

The peptide of formula 1 can be extended (shown as included in Z) at the C-terminus (but not the N-terminus) by further amino acid sequence to comprise a noninterfering substituent.

At the C-terminus of the compounds of formula 1, the carboxyl group may be in the underivatized form or may be amidated or may be an ester; in the underivatized form the carboxyl my be as a free acid or a salt, preferably a pharmaceutically acceptable salt.

If the C-terminus is amidated, the nitrogen atom of the amido group, covalently bound to the carbonyl carbon at the C-terminus, will be NR'R', wherein each R' is independently hydrogen or is a straight or branched chain alkyl of 1–6C, such alkyls are 1–6C straight- or branched-chain saturated hydrocarbyl residues, such as methyl, ethyl, isopentyl, n-hexyl, and the like. Representatives of such amido groups are: —NH₂, —NHCH₃, —N(CH₃)₂, —NHCH₂CH₃, —NHCH₂CH(CH₃)₂, and —NHCH₂CH(CH₃)CH₂CH₃, among others. Furthermore, either or both R' may in turn optionally be substituted by one or more substituents such as, for example, —OR', —NR'R', halo, —NR'CNR'NR'R' and the like, wherein each R' is as independently defined above. Thus, Z my be —OH, or an ester (OR') or salt forms thereof, or —NR'R' wherein R' is as above defined.

Preferred embodiments of AA₁ are Ser on 2,3-diaminopropionyl (2,3-diaP). Preferred embodiments of AA₂ and AA₃ are Val, Ile, Cha and Leu. Preferred embodiments for the residues in the reminder of the compound of formula (1) are those wherein AA₄ is Gly, AA₅ is Lye, Arg or Har, AA₆, if present, is Val, Ile, Cha or Leu, and AA₇, if present, is Asp or Glu. Particularly preferred are compounds of formula (1) which are selected from the group consisting of SLIGRLETQPPIT (SEQ ID NO: 32), SLIGRLETQPPI (SEQ ID NO: 33), SLIGRLETQPP (SEQ ID NO: 34), SLIGRLETQP (SEQ ID NO: 35), SLIGRLETQ (SEQ ID NO: 36), SLIGRLET (SEQ ID NO: 37), SLIGRLE (SEQ ID NO: 38), SLIGRL (SEQ ID NO: 39), SLIGR (SEQ ID NO: 40), SLLGKVDGTSHVT (SEQ ID NO: 41), SLLGKVDGTSHV (SEQ ID NO: 42), SLLGKVDGTSH (SEQ ID NO: 43), SLLGKVDGTS (SEQ ID NO: 44), SLLGKVDGT (SEQ ID NO: 45), SLLGKVDG (SEQ ID NO: 46), SLLGKVD (SEQ ID NO: 47), SLLGKV (SEQ ID NO: 48), SLLGK (SEQ ID NO: 49), S(Cha) IGR (SEQ ID NO: 50), S(Cha)LGK (SEQ ID NO: 51), (2,3-diaP)-IGR (SEQ ID NO: 52), (2,3-diaP)LLGK (SEQ ID NO: 53), SLLGKR-NH₂ (SEQ ID NO: 54), SLIGRR-NH₂ (SEQ ID NO: 55), S(Cha)LGKK-NH₂ (SEQ ID NO: 56), S(Cha)IGRK-NH₂ (SEQ ID NO: 57), (2,3-diaP)LIGRK-NH₂ (SEQ ID NO: 58), (2,3-diaP)-LLGKK-NH₂ (SEQ ID NO: 59) and the amidated forms thereof.

B. Antagonists

Compounds of the invention which interfere with activities mediated by the C140 receptor include modified agonist peptides lacking the N-terminal serine residue; and antibodies which are immunoreactive with various critical positions on the C140 receptor.

Peptide Antagonists

The antagonists of the first group-modified agonists—can be represented by the formula:

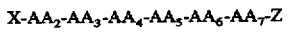

wherein X is an amino acid residue other than ser, ala, thr, cys, 2,3-diaP or gly or is a desamino or alkylated or acylated amino acid, wherein AA₂ and AA₃ are each independently neutral/nonpolar/large/nonaromatic amino acids;

AA₄ is a small amino acid;

AA₅ is a basic amino acid;

AA₆ may be present or absent and, if present, is a neutral/nonpolar/large/nonaromatic amino acid;

AA₇ is absent if AA₆ is absent and may be present or absent if AA₆ is present, and is an acidic amino acid; and Z is a substituent that does not interfere with agonist activity.

Preferred acyl groups are of the formula RCO- wherein R represents a straight or branched chain alkyl of 1–6C. Acetyl is particularly preferred.

Preferred embodiments of X include residues of 3-mercaptopropionic acid (Mpr), 3-mercaptovaleric acid (Mvl), 2-mercaptobenzoic acid (Mba) and S-methyl-3-mercaptopropionic acid (SMeMpr). Preferred embodiments for AA₂ through AA₇ are as described for the agonists above; Z is also as thus described.

Particularly preferred among the antagonist peptides of this class are those selected from the group consisting of Mpr-LLGK (SEQ ID NO: 9), Mpr-LIGR (SEQ ID NO: 10), Mpr-(Cha)LKG (SEQ ID NO: 11), Mpr-(Cha)IGR (SEQ ID NO: 12), Mpr-LLGKK-NH₂ (SEQ ID NO: 13), Mpr- LIGRK-NH$_2$ (SEQ ID NO: 14), Mpr-LIGRKETQP-NH$_2$ (SEQ ID NO: 15), Mpr-LLGKKDGTS-NH$_2$ (SEQ ID NO: 16), (n-pentyl)$_2$-N-Leu-Ile-Gly-Arg-Lys-NH$_2$ (SEQ ID NO: 17), and (Me-N-(n-pentyl)-Leu-Ile-Gly-Arg-Lys-NH$_2$ (SEQ ID NO: 18).

Antibodies

Antagonists which are antibodies immunoreactive with critical positions of the C140 receptor are obtained by immunization of suitable mammalian subjects with peptides containing as antigenic regions those portions of the C140 receptor intended to be targeted by the antibodies. Critical regions include the region of proteolytic cleavage, the segment of the extracellular segment critical for activation (this includes the cleavage site), and the portions of the sequence which form the extracellular loops, in particular, that region which interacts with the N-terminus of the activated receptor extracellular region. The agonist peptides of the invention may be used as immunogens in this case.

Thus, peptides which contain the proteolytic region, namely, for example, SKGRSLIGRLET (SEQ ID NO: 19), the extracellular loops, such as those including ISY HLH-GNNWVYGEALC (SEQ ID NO: 20); QTTYIPALNIT-TCHDVLPEEVLVGDMFNYFL (SEQ ID NO: 21); and HYFLIKTQRQSHVYA (SEQ ID NO: 22). The agonist peptides described below are also useful as immunogens.

The antibodies are prepared by immunizing suitable mammalian hosts in appropriate immunization protocols using the peptide haptens alone, if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten peptides can be extended at the amino or carboxy terminus with a Cys residue or interspersed with cysteine residues, for example, to facilitate linking to carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein or modifications which effect immortalization of lymphocytes or spleen cells, as is generally known. The immortalized cell lines secreting the desired antibodies are screened by immunoassay in which the antigen is the peptide hapten or is the C140 receptor itself displayed on a recombinant host cell. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin.

The antibodies or fragments may also be produced, using current technology, by recombinant means. Regions that bind specifically to the desired regions of receptor can also be produced in the context of chimeras with multiple species origin.

The antibodies thus produced are useful not only as potential antagonists for the receptor, filling the role of antagonist in the assays of the invention, but are also useful in immunoassays for detecting the activated receptor. As such these antibodies can be coupled to imaging agents for administration to a subject to allow detection of localized antibody to ascertain the position of C140 receptors in either activated or unactivated form. In addition, these reagents are useful in vitro to detect, for example, the successful production of the C140 receptor deployed at the surface of the recombinant host cells.

Preparation of Peptide Agonists and Antagonists

The peptide agonists and antagonists of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Preparation of C140 Receptor Nucleic Acids

C140 receptor "nucleic acid" is defined as RNA or DNA that encodes a C140 receptor, or is complementary to nucleic acid sequence encoding a C140 receptor, or hybridizes to such nucleic acid and remains stably bound to it under stringent conditions, or encodes a polypeptide sharing at least 75% sequence identity, preferably at least 80%, and more preferably at least 85%, with the translated amino acid sequences shown in FIGS. 3, 10A–10B or 11A–11B. It is typically at least about 10 nucleotides in length and preferably has C140 receptor biological or immunological activity, including the nucleic acid encoding an activation peptide fragment having the nucleotide sequence shown in FIG. 4. Specifically contemplated are genomic DNA, cDNA, mRNA and antisense molecules, as well as nucleic acids based on alternative backbone or including alternative bases whether derived from natural sources or synthesized. Such hybridizing or complementary nucleic acid, however, is defined further as being novel and unobvious over any prior art nucleic acid including that which encodes, hybridizes under stringent conditions, or is complementary to nucleic acid encoding a known G protein-coupled receptor.

"Stringent conditions" are those that (1) employ low ionic strength and high temperature for washing, for example, 0.015M NaCl/0.0015M sodium titrate/0.1% NaDodSO4 at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 mu g/ml), 0.1% SDS, and 10% dextran sulfate at 42° C., with washes at 42° C. in 0.2×SSC and 0.1% SDS.

"Isolated" nucleic acid will be nucleic acid that is identified and separated from contaminant nucleic acid encoding other polypeptides from the source of nucleic acid. The nucleic acid my be labeled for diagnostic and probe purposes, using any label known and described in the art as useful in connection with diagnostic assays.

Of particular interest is a C140 receptor nucleic acid that encodes a full-length molecule, including but not necessarily the native signal sequence thereof. Nucleic acid encoding full-length protein is obtained by screening selected cDNA (not kidney) or genomic libraries using the deduced amino acid sequence disclosed herein for the first time, and, if necessary, using conventional primer extension procedures to secure DNA that is complete at its 5' coding end. Such a clone is readily identified by the presence of a start codon in reading frame with the original sequence.

DNA encoding an amino acid sequence variant of a C140 receptor is prepared as described below or by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of a C140 receptor.

Techniques for isolating and manipulating nucleic acids are disclosed for example by the following documents: U.S. Pat. No. 5,030,576, U.S. Pat. No. 5,030,576 and International Patent Publications WO94/11504 and WO93/03162. See, also, Sambrook, J. et al., *Molecular Cloning: A Laboratory Manual*, 2nd Edition, Cold Spring Harbor Press, Cold Spring Harbor, N.Y., 1989, and Ausubel, F. M. et al. *Current Protocols in Molecular Biology*, Vol. 2, Wiley-Interscience, New York, 1987. Disclosures of these documents are expressly incorporated herein by reference in their entireties.

Recombinant Production of C140 Receptor for Use in Assays

The invention provides recombinant materials for the production of C140 receptor for display on the surface of recombinant cells. Production of the receptor using these recombinant methods provides a useful reagent to determine the ability of a candidate drug to bind to, to activate, or to antagonize the C140 receptor. Determination of these properties is essential in evaluating the specificity of drugs intended for binding other related receptors.

For this recombinant production, a DNA sequence encoding the C140 receptor, such as those set forth in FIGS. 1A–1B and 2A–2B, or their substantial equivalents or their degenerate analogs, is prepared either by retrieval of the native sequence, as set forth below, or by using substantial portions of the known native sequence as probe, or can be synthesized de novo using standard procedures. The DNA is ligated into expression vectors suitable for the desired host and transformed into compatible cells. The cells are cultured under conditions which favor the expression of the C140 receptor encoding gene and the cells displaying the receptor on the surface are harvested for use in the assays.

The host cells are typically animal cells, most typically mammalian cells. In order to be useful in the assays, the cells must have intracellular mechanisms which permit the receptor to be displayed on the cell surface in the configuration shown generally in FIG. 4 herein. If the assay uses cellular response to activated receptor as a detection system, the cells must also contain a G-protein linked mechanism for response to activation of the receptors. Most mammalian and other animal cells fulfill these qualifications.

Particularly useful cells for use in the method of the invention are *Xenopus laevis* frog oocytes, which typically utilize cRNA rather than standard recombinant expression systems proceeding from the DNA encoding the desired protein. Capped RNA (at the 5' end) is typically produced from linearized vectors containing DNA sequences encoding the receptor. The reaction is conducted using RNA polymerase and standard reagents. cRNA is recovered, typically using phenol/chloroform precipitation with ethanol and injected into the oocytes.

The animal host cells expressing the DNA encoding the C140 receptor or the cRNA-injected oocytes are then cultured to effect the expression of the encoding nucleic acids so as to produce the C140 receptor displayed in a manner analogous to that shown in FIG. 4 on their surfaces. These cells then are used directly in assays for assessment of a candidate drug to bind, antagonize, or activate the receptor.

Assays

In one type of easily conducted assay, competition of the candidate drug for binding to the receptor with either agonist or known binding antagonist can be tested. In one method, the competing agonist or antagonist may be labeled; the labeled substance known to bind the receptor can, of course, be a synthetic peptide. In one typical protocol, varying concentrations of the candidate are supplied along with a constant concentration of labeled agonist or antagonist and the inhibition of a binding of label to the receptor can be evaluated using known techniques.

In a somewhat more sophisticated approach, the effect of candidate compounds on agonist-induced responses can be measured in the cells recombinantly expressing the C140 receptor as described below. Assay systems for the effect of activation of receptor on these cells include calcium mobilization and voltage clamp which are described herein in further detail. These assays permit an assessment of the effect of the candidate drug on the receptor activity rather than simply ability to bind to the receptor.

Agonist-induced increases in $^{45}$Ca release by oocytes expressing cRNA encoding C140 receptor or other recombinant cells producing C140 receptor are assessed by published techniques (Williams, J. A., et al., *Proc Natl Acad Sci USA* (1988) 85:4939–4943). Briefly, intracellular calcium pools are labeled by incubating groups of 30 oocytes in 300 µl calcium-free modified Barth's solution (MBSH) containing 50 µCi $^{45}$CaCl$_2$ (10–40 mCi/mg Ca; Amersham) for 4 hours at RT. The labeled oocytes or cells are washed, then incubated in MBSH II without antibiotics for 90 minutes. Groups of 5 oocytes are selected and placed in individual wells in a 24-well tissue culture plate (Falcon 3047) containing 0.5 ml/well MBSH II without antibiotics. This medium is removed and replaced with fresh medium every 10 minutes; the harvested medium is analyzed by scintillation counting to determine $^{45}$Ca released by the oocytes during each 10-minute incubation. The 10-minute incubations are continued until a stable baseline of $^{45}$Ca release per unit time is achieved. Two additional 10-minute collections are obtained, then test medium including agonist is added and agonist-induced $^{45}$Ca release determined.

Using the above assay, the ability of a candidate drug to activate the receptor can be tested directly. In this case, the agonists of the invention are used as controls. In addition, by using the agonist of the invention to activate the recombinant receptor, the effect of the candidate drug on this activation can be tested directly. Recombinant cells expressing the nucleic acids encoding the receptor are incubated in the assay in the presence of agonist with and without the candidate compound. A diminution in activation in the presence of the candidate will indicate an antagonist effect. Conversely, the ability of a candidate drug to reverse the antagonist effects of an antagonist of the invention may also be tested.

In an alternative to measuring calcium mobilization, the voltage clamp assay can be used as a measure for receptor activation. Agonist-induced inward chloride currents are measured in voltage-clamped oocytes expressing C140 receptor encoding cRNA or cells expressing DNA from recombinant expressions systems essentially as previously described (Julius, D., et al, *Science* (1988) 241:558–563) except that the single electrode voltage-clamp technique is employed.

Detection of Activated Receptors

In one embodiment, the availability of the recombinant C140 receptor protein permits production of antibodies which are immunospecific to the activated form of the receptor which can then be used for diagnostic imaging of activated receptors in vivo. These antibodies are produced either to the activated form of the receptor produced recombinantly, or to the peptide representing the "new amino terminal" peptide described herein. The resulting antibodies, or the immunospecific fragments thereof, such as the Fab, Fab', Fab'$_2$ fragments are then conjugated to labels which are detected by known methods, such as radiolabels including technetium[99] and indium[111] or other radioactive labels as is known in the art. When injected in vivo, these antibodies home to the sites of activated receptor, thus permitting localization of areas containing activated receptors.

In another embodiment, the presence of the activation peptide in body fluids or in culture media can be detected and measured. Antibodies are made to the activation peptide as described above and can be employed in standard ELISA or RIA assays to detect excess amounts of the activation peptide in, for example, urine.

Administration of Agonists and Antagonists as Pharmaceuticals

The peptides of the invention which behave as agonists are administered in conventional formulations for systemic administration as is known in the art. Typical such formulations may be found, for example, in *Remington's Pharmaceutical Sciences*, Mack Publishing Co., Easton Pa., latest edition.

Preferred forms of systemic administration of peptides include injection, typically by intravenous injection. Other injection routes, such as subcutaneous, intramuscular, or intraperitoneal, can also be used. More recently, alternative means for systemic administration of peptides have been devised which include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the patient's condition, and the judgment of the attending physician. Suitable dosage ranges, however, are in the range of 0.1–100 μg/kg of subject. Wide variations in the needed dosage, however, are to be expected in view of the variety of peptides available and the differing efficiencies of various routes of administration. For example, oral administration would be expected to require higher dosages than administration by intravenous injection. Variations in these dosage levels can be adjusted using standard empirical routines for optimization as is well understood in the art.

As shown hereinbelow, the agonists of the invention behave as antihypotensives; antagonists have the opposite effect. Thus, patients whose blood pressure needs to be raised or lowered benefit by the administration of the suitable peptide.

In addition, the agonists have anti-inflammatory and wound healing properties.

Antisense, Triple Helix and Gene Therapy Aspects

The constitutive expression of antisense RNA in cells has been shown to inhibit the expression of about 20 different genes in mammals and plants, and the list continually grows (Hambor, J. E. et al., J. Exp. Med. 168:1237–1245 (1988); Holt, J. T. et al., Proc. Nat. Acad. Sci. 83:4794–4798 (1986); Izant, J. G. et al., Cell 36:1007–1015 (1984); Izant, J. G., et al., Science 229:345–352 (1985) and De Benedetti, A. et al., Proc. Nat. Acad. Sci. 84:658–662 (1987)). Possible mechanisms for the antisense effect are the blockage of translation or prevention of splicing, both of which have been observed in vitro. Interference with splicing allows the use of intron sequences (Munroe, S. H., EMBO. J. 7:2523–2532 (1988) which should be less conserved and therefore result in greater specificity in inhibiting expression of a protein of one species but not its homologue in another species.

Therapeutic gene regulation is accomplished using the "antisense" approach, in which the function of a target gene in a cell or organism is blocked, by transfection of DNA, preferably an oligonucleotide, encoding antisense RNA which acts specifically to inhibit expression of the particular target gene. The sequence of the antisense DNA is designed to result in a full or preferably partial antisense RNA transcript which is substantially complementary to a segment of the gene or mRNA which it is intended to inhibit. The complementarity must be sufficient so that the antisense RNA can hybridize to the target gene (or mRNA) and inhibit the target gene's function, regardless of whether the action is at the level of splicing, transcription or translation. The degree of inhibition, readily discernible by one of ordinary skill in the art without undue experimentation, must be sufficient to inhibit, or render the cell incapable of expressing, the target gene. One of ordinary skill in the art will recognize that the antisense RNA approach is but one of a number of known mechanisms which can be employed to block specific gene expression.

By the term "antisense" is intended an RNA sequence, as well as a DNA sequence coding therefor, which is sufficiently complementary to a particular mRNA molecule for which the antisense RNA is specific to cause molecular hybridization between the antisense RNA and the mRNA such that translation of the mRNA is inhibited. Such hybridization must occur under in vivo conditions, that is, inside the cell. The action of the antisense RNA results in specific inhibition of gene expression in the cell. (See: Alberts, B. et al., *MOLECULAR BIOLOGY OF THE CELL*, 2nd Ed., Garland Publishing, Inc., New York, N.Y. (1989), in particular, pages 195–196.

The antisense RNA of the present invention may be hybridizable to any of several portions of a target mRNA, including the coding sequence, a 3' or 5' untranslated region, or other intronic sequences. A preferred antisense RNA is that complementary to the human C140 receptor mRNA. As is readily discernible by one of skill in the art, the minimal amount of homology required by the present invention is that sufficient to result in hybridization to the specific target mRNA and inhibition of its translation or function while not affecting function of other mRNA molecules and the expression of other genes.

Antisense RNA is delivered to a cell by transformation or transfection with a vector into which has been placed DNA encoding the antisense RNA with the appropriate regulatory sequences, including a promoter, to result in expression of the antisense RNA in a host cell.

"Triple helix" or "triplex" approaches involve production of synthetic oligonucleotides which bind to the major groove of a duplex DNA to form a colinear triplex. Such triplex formation can regulate and inhibit cellular growth. See, for example: Hogan et al., U.S. Pat. No. 5,176,996; Cohen, J. S. et al., *Sci. Amer.*, December 1994, p. 76–82; Helene, C., *Anticancer Drug Design* 6:569–584 (1991); Maher III, L. J. et al., *Antisense Res. Devel.* 1:227–281 (Fall 1991); Crook, S. T. et al. eds., ANTISENSE RESEARCH AND APPLICATIONS, CRC Press, 1993. It is based in part on the discovery that a DNA oligonucleotide can bind by triplex formation to a duplex DNA target in a gene regulatory region, thereby repressing transcription initiation (Cooney M. et. al. (1988) *Science* 241:456). The present invention utilizes methods such as those of Hogan et al., supra (herein incorporated by reference in its entirety), to designing oligonucleotides which will bind tightly and specifically to a duplex DNA target comprising part of the C140 receptor-encoding DNA or a regulatory sequence thereof. Such triplex oligonucleotides can therefore be used as a class of drug molecules to selectively manipulate the expression of this gene.

Thus the present invention is directed to providing to a cell or administering to a subject a synthetic oligonucleotide in sufficient quantity for cellular uptake and binding to a DNA duplex of the target C140 receptor-coding DNA sequence or a regulatory sequence thereof, such that the oligonucleotide binds to the DNA duplex to form a colinear triplex. This method is used to inhibit expression of the receptor on cells in vitro or in vivo. Preferably the target sequence is positioned within the DNA domain adjacent to the RNA transcription origin. This method can also be used to inhibit growth of cells which is dependent on expression of this receptor. The method may also be used to alter the relative amounts or proportions of the C140 receptor expressed on cells or tissues by administering such a triplex-forming synthetic oligonucleotide.

The following examples are intended to illustrate but not to limit the invention.

EXAMPLE 1

Isolation of the Gene Encoding Murine C140 Receptor

A mouse cosmid genomic library (obtained from Dr. R. A. Wetsel, Washington University School of Medicine, St. Louis, Mo. and described in Wetsel, R. A. et al., *J Biol Chem* (1990) 265:2435–2440) was screened with two $^{32}$P-labeled oligonucleotides corresponding to bp 190–249 and 742–801, respectively, of the bovine substance K receptor cDNA (Masu, Y. et al., *Nature* (1987) 329:836–838). The hybridization conditions are 5×SSC, 5×Denhardt's, 0.1% SDS, 0.1 mg/ml sperm DNA, $10^6$ cpm/ml of labeled oligonucleotides, 60° C. overnight, followed by washing with 1×SSC, 0.1% SDS at 60° C.

In one of the clones isolated (C140) the hybridizing region was localized to a 3.7 kb PstI fragment. This fragment was subcloned into the commercially available pBluescript vector. The hybridizing and adjacent regions were sequenced in both orientations by the Sanger chain termination method. FIGS. 1A–1B shows both the nucleotide sequence and the deduced amino acid sequence of the mouse C140 receptor. The tentative signal sequence (SP) and the seven transmembrane regions are overlined, potential asparagine-linked glycosylation sites are marked with bold arrows, and the putative protease receptor cleavage site at Arg34-Ser35 is marked with an open arrow.

EXAMPLE 2

Isolation of the Gene Encoding Human C140 Receptor

The availability of genomic DNA encoding the mouse protease C140 receptor permitted the retrieval of the corresponding human gene. A human genomic library cloned in the vector EMBL3 was screened at exactly the conditions in Example 1 using the entire coding region of the murine clone as a probe. The recovered human gene including the DNA sequence and the deduced amino acid sequence are shown in FIGS. 2A–2B. Subsequent experiments indicated that the human C140 gene is located in the same region of the long arm of chromosome number 5 (Sq12–Sq13) as has been reported for the human thrombin receptor gene.

In addition, a 1.1 kb genomic DNA fragment was obtained from Genome Systems Inc., commercial screening service as was PCR-positive with a primer pair that generates a fragment spanning 350-nucleotides of the human C140 protein coding region. A 1.1 kb bamH1 fragment was subcloned and sequenced and found to contain 800-nucleotides of promoter sequence. The promoter lacks both a TATA box and a CAAT box but is rich in G's and C's; features common to promoters of many housekeeping genes. Two binding elements specific for SP1 and AP2 were identified.

EXAMPLE 3

Comparison of Related G-Protein Receptors

As shown in FIG. 3, the deduced amino acid sequence of the human protease C140 receptor shows extensive similarity (>90%) to the mouse sequence.

FIG. 5 shows an amino acid sequence alignment between the mouse C140 receptor and the related G-protein receptor human thrombin receptor Vu, T. et. al., *Cell* (1991) 64:1051–1068. The tentative signal sequences (SP), transmembrane regions, and protease cleavage sites are marked.

EXAMPLE 4

Recovery of Mouse C140 cDNA

A cDNA library from a mouse stomach was constructed in λ gt10 and screened with a probe encompassing the C1040 genomic DNA. A single phage clone was isolated and cut with EcoRI. The insert was cloned into pBluescript and pSG5 and sequenced.

The isolated cDNA was 2732 nucleotides long including a 16 base polyA-stretch; 5' RACE resulted in the addition of only 27 bases to the 5' end. The 5' end of the apparent coding region differs from the 5' end of the open reading frame of genomic DNA; it is believed that the 5' end of the cDNA is correct. The complete nucleotide sequence and deduced amino acid sequence of murine cDNA encoding C140 is shown in FIGS. 10A–10B.

EXAMPLE 5

Recovery of Human cDNA Encoding C140

A human intestinal tumor cDNA library was subjected to PCR using primers designed from the genomic clone of Example 2 and the amplified fragment was cloned in pSG5 and sequenced. The nucleotide sequence and deduced amino acid sequence are shown in FIGS. 11A–11B. There are four amino acid differences between the cDNA encoded sequence and that encoded by the genomic DNA as is shown in FIGS. 11A–11B.

EXAMPLE 6

Activation of Protease C140 Receptor in Oocytes

Both native and mutant C140 receptors were produced in oocytes and activated with a peptide mimicking the new amino-terminus", or by the proteolytic enzyme trypsin (which cleaves the extracellular region). Native receptors were produced by cloning the coding region of the receptor gene, using the polymerase chain reaction, into the expression vector pSG-5 (Green, S. et al., *Nucleic Acid Res* (1988) 16:369). The orientation and integrity of the cloned coding region was verified by determining the nucleotide sequence with the Sanger chain-termination method. Site-directed mutagenesis was employed to construct mutant receptors in the pSG-5. Three mutant receptors were made, in which serine-35 was replaced with proline, arginine, and histidine, respectively. The nucleotide sequences of the three mutants was verified as above.

In order to produce the receptor at the surface of oocytes, cRNA encoding the receptor was produced as follows. pSG-5 C140 plasmid DNA was made linear by digestion with XbaI, and capped cRNA was produced in vitro using T7 RNA polymerase (Krieg and Melton, *Meth Enzymol* (1987) 155:397–415, which reference is hereby incorporateds by reference in its entirety).

Oocytes from *Xenopus laevis* were harvested and prepared using published techniques (Coleman, A., in Hames, B. D., and Higgins, S. J., eds, *Transcription and Translation: A Practical Approach*, IRL Press, pp. 271–302; Williams, J. A., et al. *Proc Natl Acad Sci USA* (1988) 85:4939–4943]. To remove follicular cells, oocytes were incubated for 1.5 h with shaking in calcium-free Barth's containing 2 mg/ml each of collagenase 1A and hyaluronidase 1S. The oocytes were then washed five times in regular Barth's and incubated at 18° C. in Barth's medium containing 100 U/ml penicillin, 100 µg/ml streptomycin, and 2.5 mM sodium pyruvate. Stage V oocytes were selected and injected with 30 nl of cRNA (0.33 µg/µl water) or water alone, and then incubated with 0.25 ml of medium in groups of four/well in a 96-well culture plate. After 36 hours the oocytes were incubated with $^{45}$Ca (250 µCi/ml). After 12 h incubation the oocytes were washed and 0.2 ml of medium added and replaced every five minutes. The harvested medium was analyzed by scintillation counting. After five replacements to determine the baseline release of $^{45}$Ca, test medium with the agonist, e.g. SLIGRL (SEQ ID NO: 23), was added and the evoked $^{45}$Ca-release determined.

Oocytes were injected with capped cRNA (ca 10 ng) encoding wild-type mouse C140 receptor (WT) or either of the three mutant receptors 35Pro, 35Arg and 35His. After 36 hours, cRNA-injected and control water-injected, oocytes were loaded with $^{45}$Ca, and 12 hours thereafter peptide or trypsin-induced $^{45}$Ca release were determined as described above. The peptide SLIGRL (SEQ ID NO: 23) was added at 100 µM, and trypsin at 300 pM. The stimulation with the peptide was done on the same group of oocytes after the stimulation with trypsin. The data shown in Table 1 represent the mean of three replicate determinations, and denotes the increase compared to oocytes injected with water.

TABLE 1

| Receptor | Agonist | Fold increase in $^{45}$Ca |
|---|---|---|
| WT | Trypsin | 6.6 |
| 35Pro | Trypsin | 0 |
| 35Arg | Trypsin | 0 |
| 35His | Trypsin | 0 |
| WT | SLIGRL (SEQ ID NO:23) | 11 |
| 35Pro | SLIGRL (SEQ ID NO:23) | 23 |

TABLE 1-continued

| Receptor | Agonist | Fold increase in $^{45}$Ca |
|---|---|---|
| 35Arg | SLIGRL (SEQ ID NO:23) | 15 |
| 35His | SLIGRL (SEQ ID NO:23) | 23 |

As shown in Table 1, the agonist peptide SLIGRL (SEQ ID NO: 23) was able to activate both the wild-type and mutated receptors. On the other hand, trypsin, which can activate only by cleavage of the extracellular domain, is able only to activate the wild-type receptor.

EXAMPLE 7

Activation of the C140 Receptor by Different Agonist Peptides

Various peptides were tested at 100 µM in the assay above using wild-type mouse C140 receptor, expressed in oocytes. The results are shown in Table 2.

TABLE 2

| Peptide | Fold Increase in $^{45}$Ca |
|---|---|
| SLIGRL (SEQ ID NO:23) | 15 |
| SLIGRA (SEQ ID NO:24) | 8.5 |
| SLIGAL (SEQ ID NO:25) | 0 |
| SLIARL (SEQ ID NO:26) | 4.3 |
| SLAGRL (SEQ ID NO:27) | 0 |
| SAIGRL (SEQ ID NO:28) | 0 |
| ALIGRL (SEQ ID NO:29) | 1.3 |
| SFFLRW (SEQ ID NO:30) | 1.7 |

The "native" peptide SLIGRL (SEQ ID NO: 23) is most effective; replacing L at position 6 with alanine lowers but does not destroy activity. Positions 2 and 3 are more sensitive. Position 1 tolerates substitution with alanine but decreases the activity by a factor of 10; the activity of this agonist is comparable to the analogous thrombin receptor agonist SFFLRW (SEQ ID NO: 30).

EXAMPLE 8

Expression of C140 Receptor in Various Tissues

Poly(A)+RNA was prepared from mouse tissues, resolved on a 1.2% agarose gel containing 50% formamide and blotted onto Hybond C extra membrane (Amersham). The blot was hybridized with a $^{32}$P-labeled "random priming probe" directed against the whole coding region of murine C140 receptor. The probe was hybridized at 42° C. for 48 hr then successively washed at 20° C. in 1×SSC, 0.1% SDS twice, 5 min each time, then at 65° C. in 1×SSC, again twice for 20 min each time, and then 0.1×SSC, 0.1% SDS twice for 20 min each time. The resulting membrane was autoradiographed for 5 days at −80° C. with an intensifying screen.

Figure 6:
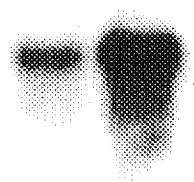
FIG. 6 shows the results of Northern Blot to detect the presence of mRNA encoding C140 receptor in various mouse tissues.

The results, shown in FIG. 6 indicate that kidney and small intestine, but not spleen, contain mRNA encoding C140. In FIG. 6, where each lane contains 10 µg RNA, lane A is derived from spleen, lane B from kidney and lane C from small intestine.

EXAMPLE 9

Expression of C140 Transcripts In Mice

In situ hybridization using $^{35}$S RNA probes was used to localize C140 transcripts in mouse embryogenesis and in adult mouse tissues. A strong signal was found in the gastrointestinal tract at 11.5 days; at 14 days there was strong hybridization to epithelial structures in the nasopharynx, stomach-intestine, skin and endothelial cells in larger vessels. There was some hybridization in the liver and sclerotoma but no signal in muscle or CNS. At 17 days, the signals in the sclerotoma had disappeared and additional epithelial structures showed hybridization including the esophagus, kidney glomeruli, lung, hair follicles and epidermis.

Figure 12:
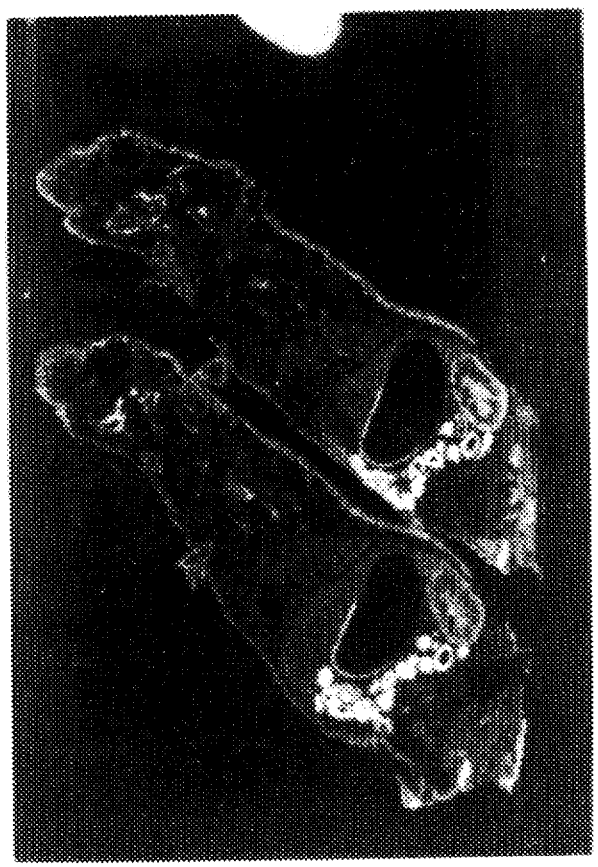
FIG. 12 shows the results of in situ hybridization of a sectioned newborn mouse with mouse C140 receptor probes.

In newborns, the signals found at 17 days were retained and additional signals were found in the thymic medulla and kidney medulla. Adults showed transcripts in the mucosa of stomach, intestine and colon, white pulp of the spleen, thymus and kidney medulla. Again, there were no signals in the CNS, liver, lung or adrenal gland. FIG. 12 shows the results of in situ hybridization in a sectioned newborn mouse using these probes.

EXAMPLE 10

Expression of C140 Transcripts In Human Tissues

Figure 13:
FIG. 13 shows a Northern blot of total RNA from human cell lines hybridized to a human C140 receptor probe.

FIG. 13 shows the results of a Northern blot of total RNA from human cell lines hybridized to a human C140 receptor probe. Ten mg of total RNA was used. Hybridization was obtained in RNA from stomach (lane 1), Ca-Co-2 cells (lane 2); HT-29 cells (lane 3), A498 cells (lane 5), 5637 cells (lane 8); skin keratinocytes (lane 12), and HUVEC (lanes 13 and 14). No hybridization was detected in HuTu80 cells, J82 cells, MCF-7, HeLa or NCI 12 cells (lanes 4, 6, 9 and 10).

EXAMPLE 11

Determination of Hypotensive Activity of C140 Agonists

The C140 agonist SLIGRL (SEQ ID NO: 23) was injected in 0.2 ml buffer at various concentrations into rat femoral vein and the arterial pressure was monitored. The results of various concentrations are shown in FIG. 7.

Figure 7:
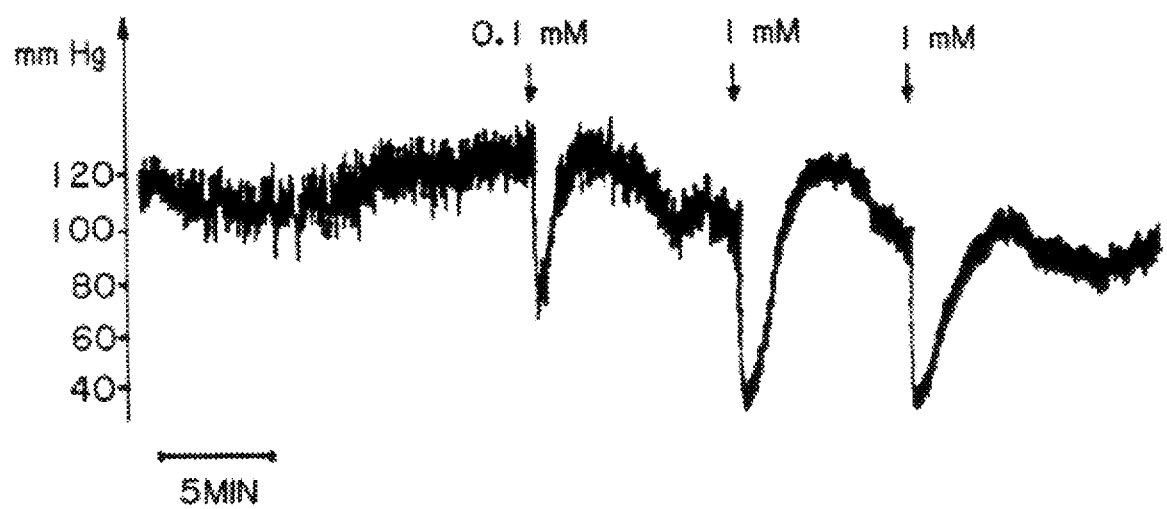
FIG. 7 shows a trace of blood pressure demonstrating the in vivo hypotensive effect of a C140 agonist peptide.

The trace in FIG. 7 shows that even at 0.1 mM an appreciable decrease in blood pressure occurred; larger decreases were observed at 1 mM concentration.

This effect was also shown by observing vasodilation as a result of stimulation of the rat femoral vein with the above agonist. Adult Sprague-Dawley rats were killed by exsanguination during diethylether anesthesia and the femoral vein was removed and dissected free from fat and connective tissue. Circular preparations of the vein were mounted in an organ bath (5 ml) on two L-formed metal holders (0.2 mm diameter). One of the metal holders was screwed into one of the levers of a Grass FTO C force displacement transducer. The bathing liquid was Kreb's Ringer solution containing 118 mM NaCl, 4.7 mM KCl, 2.5 mM $CaCl_2$, 1.2 mM $MgSO_4$, 24.8 mM $NaHCO_3$, 1.2 mM $KH_2PO_4$ and 5.6 mM glucose. The bathing fluid was continuously treated with 88.5% oxygen-11.5% $CO_2$; the temperature was held at 37° C. The endothelium was removed by bubbling $CO_2$ through the vessels. The basal tension was between 7.5 and 12 mN. The preparations were equilibrated for at least 1 hr before application of agonist and control substances.

Figure 8A:
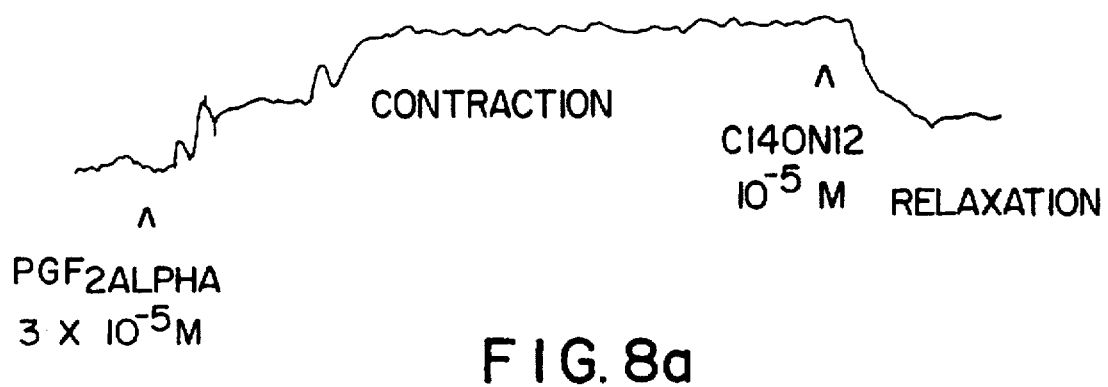
FIGS. 8a–8b show blood vessel dilation in rat femoral vein induced by a C140 receptor agonist peptide.
Figure 8B:
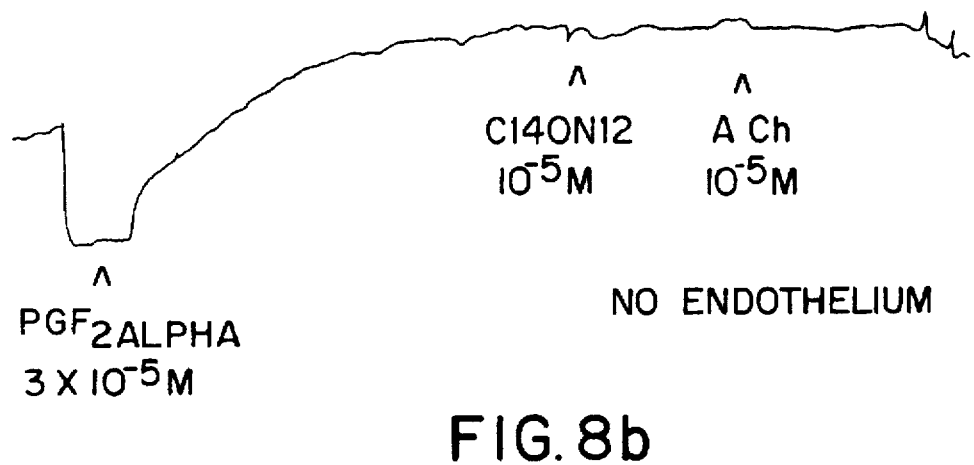

The results of these determinations are shown in FIGS. 8a and 8b. As shown in FIG. 8a, contraction induced by application of $PGF_{2\alpha}$ at $3\times10^{-5}M$ is relaxed by administration of $10^{-5}M$ agonist. The results in FIG. 8a were obtained using the vein with the endothelium still present.

In FIG. 8b, the endothelium has been removed. In an analogous experiment, the contraction induced by $3\times10^{-5}M$ $PGF_{2\alpha}$ is not counteracted by $10^{-5}M$ agonist or by $10^{-5}M$ acetylcholine.

EXAMPLE 8

Activation of Recombinant C140 Receptor by Plasmin and Kallikrein

Figure 9A:
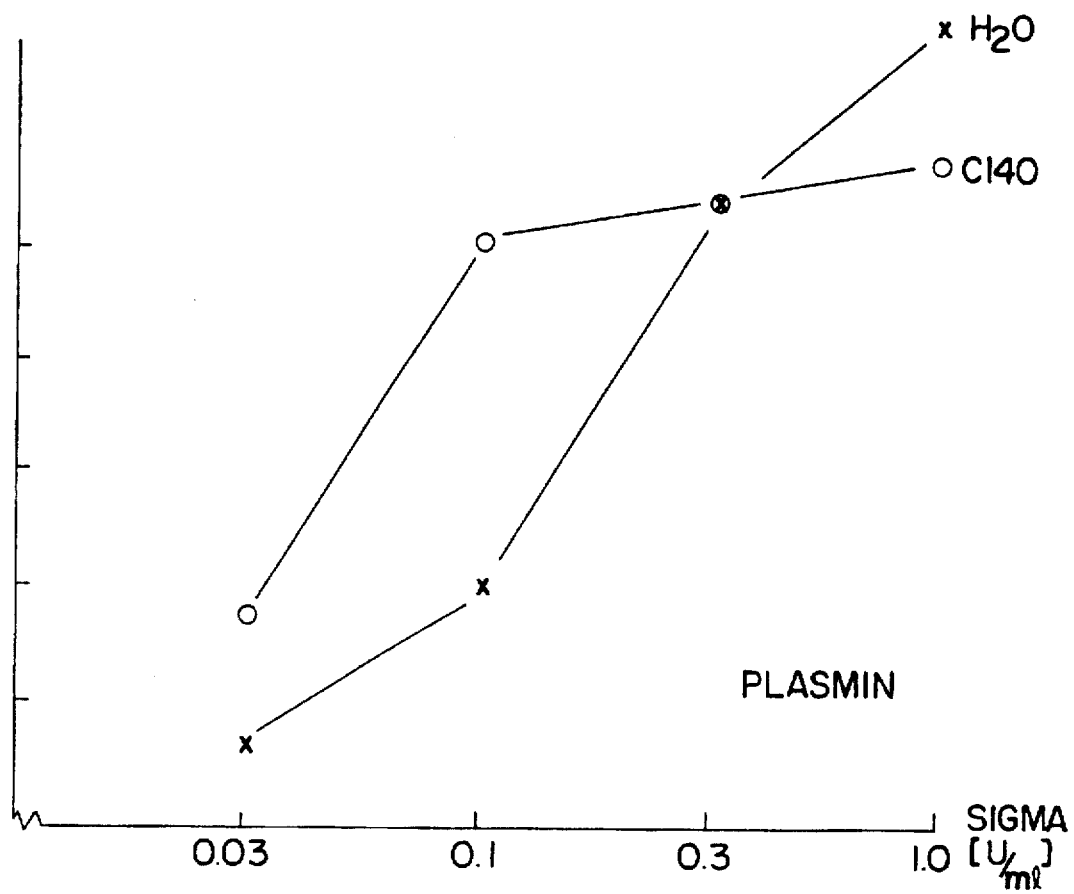
FIGS. 9a–9c show the results of an assay for activation of the C140 receptor, expressed in frog oocytes, by plasmin, kallikrein, or trypsin.
Figure 9B:
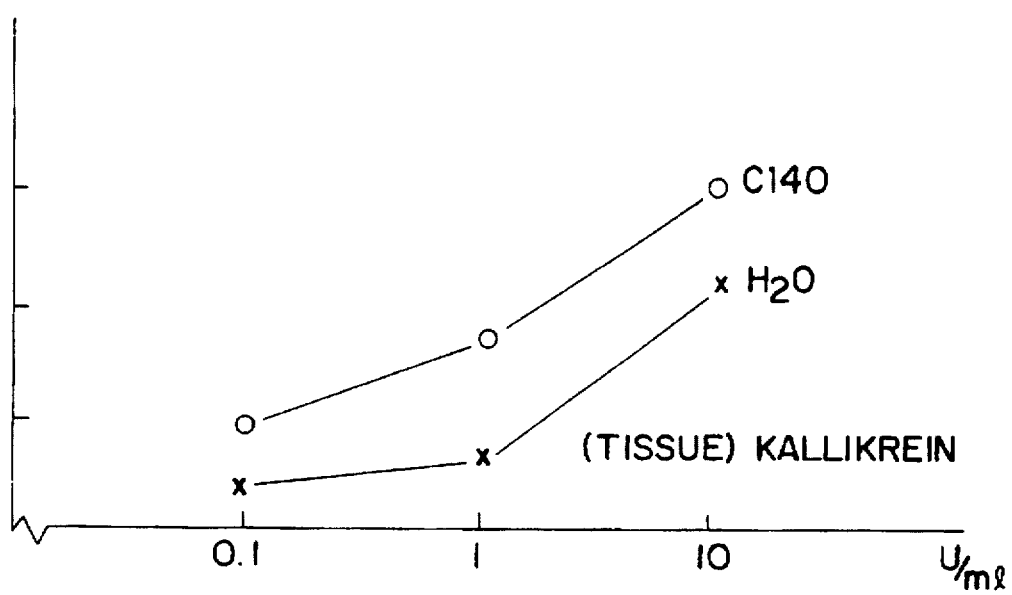
Figure 9C:
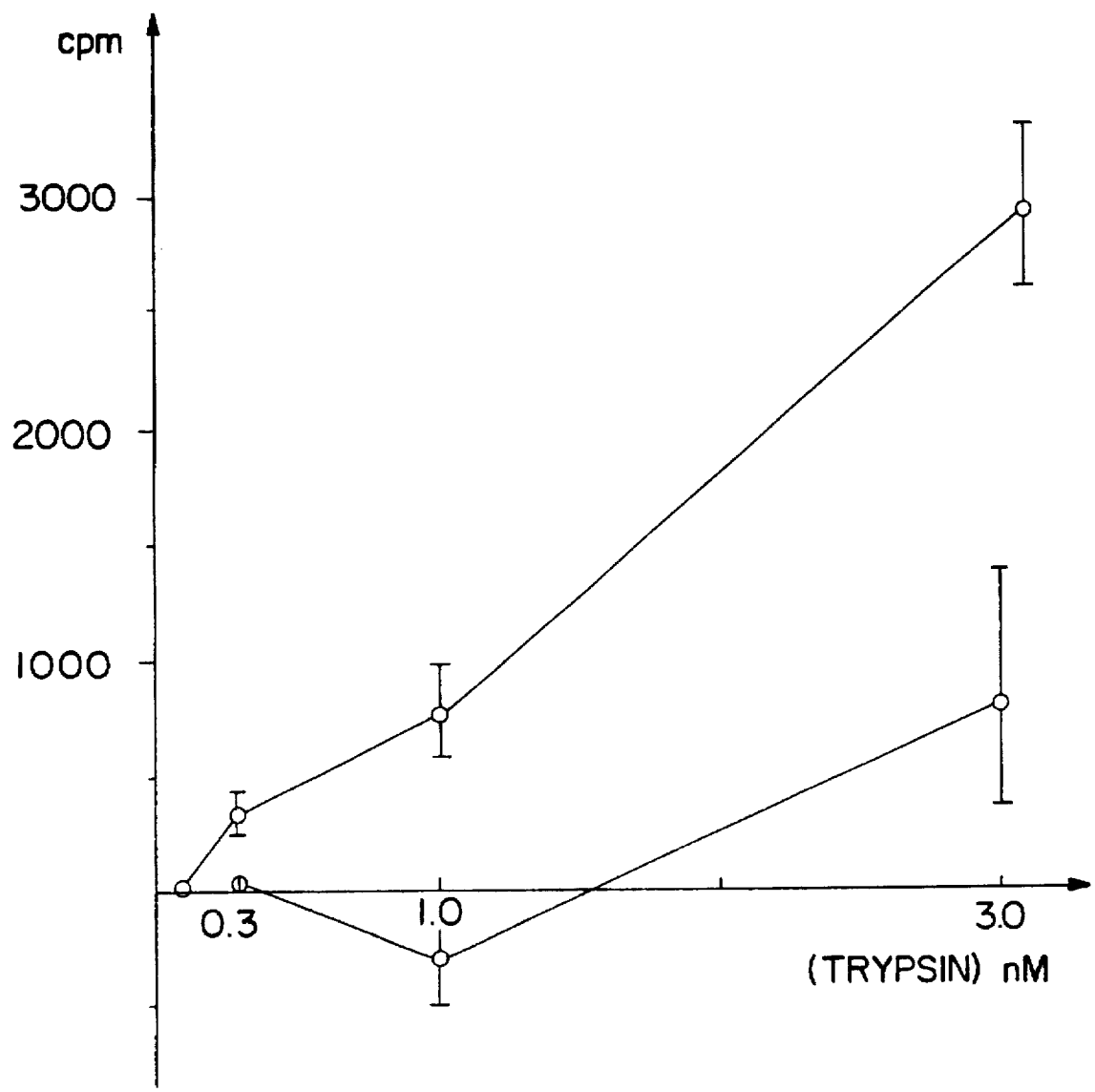

FIGS. 9a and 9b show the ability of plasmin and kallikrein respectively to activate oocytes injected with C140 cRNA (open circles) or water (crosses) as control. FIG. 9c shows the ability of trypsin to activate frog oocytes injected with C140 receptor cRNA (filled circles) or substance K receptor cRNA (open circles). Trypsin clearly has a differential effect on the C140 receptor-injected oocytes.

All references cited and mentioned above, including patents, journal articles and texts, are all incorporated by reference herein, whether expressly incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

---

We claim:

1. A method to determine the C140 agonist activity of a candidate substance, which method comprises:

incubating cells that express at their surface a C140 receptor encoded by SEQ ID NO: 1 or encoded by SEQ ID NO: 3 or encoded by a nucleotide sequence that hybridizes under conditions of 1×SSC and 0.1% SDS at 60° C. with SEQ ID NO: 1 or SEQ ID NO: 3, and which nucleotide sequence encodes a receptor which binds to a C140 ligand, in the presence and absence of the substance, and measuring the activation of the C140 receptor in the presence and in the absence of said substance, whereby an increase in said activation in the presence as compared to the absence of said substance indicates agonist activity of the substance.

2. The method of claim 1, wherein said cells have been transformed with an expression system capable of producing the C140 receptor at said cells' surface, which expression system comprises a nucleotide sequence encoding the C140 receptor operably linked to a control sequence heterologous to said encoding nucleotide and operable in said cells.

3. The method of claim 2, wherein said cells are animal cells.

4. The method of claim 3, wherein said animal cells are oocytes.

5. The method of claim 2, wherein said measuring step measures calcium mobilization or inward chloride current.

6. A method to determine the C140 antagonist activity of a candidate substance, which method comprises:

incubating cells that express at their surface a C140 receptor encoded by SEQ ID NO: 1 or encoded by SEQ ID NO: 3 or encoded by a nucleotide sequence that hybridizes under conditions of 1×SSC and 0.1% SDS at 60° C. with SEQ ID NO: 1 or SEQ ID NO: 3, and which nucleotide sequence encodes a receptor which binds to a C140 ligand, in the presence and absence of the substance, and measuring the activation of the C140 receptor in the presence and in the absence of said substance, whereby a decrease in said activation in the presence as compared to the absence of the substance indicates antagonist activity of the substance.

7. The method of claim 6, wherein said cells have been transformed with an expression system capable of producing the C140 receptor at said cells' surface, which expression system comprises a nucleotide sequence encoding the C140 receptor operably linked to a control sequence heterologous to said encoding nucleotide and operable in said cells.

8. The method of claim 7, wherein said cells are animal cells.

9. The method of claim 8, wherein said animal cells are oocytes.

10. The method of claim 7, wherein said measuring step measures calcium mobilization or inward chloride current.

11. A method to determine the C140 receptor binding activity of a candidate substance, which method comprises:

incubating cells that express at their surface a C140 receptor encoded by SEQ ID NO: 1 or encoded by SEQ ID NO: 3 or encoded by a nucleotide sequence that hybridizes under conditions of 1×SSC and 0.1% SDS at 60° C. with SEQ ID NO: 1 or SEQ ID NO: 3, and which nucleotide sequence encodes a receptor which binds to a C140 ligand, in the presence and absence of the substance, and measuring the binding of said substance to the C140 receptor.

12. The method of claim 11, wherein said cells have been transformed with an expression system capable of producing the C140 receptor at said cells' surface, which expression system comprises a nucleotide sequence encoding the C140 receptor operably linked to a control sequence heterologous to said encoding nucleotide and operable in said cells.

13. The method of claim 12, wherein said cells are animal cells.

14. The method of claim 13, wherein said animal cells are oocytes.

15. The method of claim 12, wherein said measuring step involves a competitive inhibition of binding of a labeled known agonist or antagonist.

16. The method of any of claims 1, 6 or 11, in which the hybridizing C140 receptor is encoded by a naturally occurring nucleotide sequence.

* * * * *

SEQUENCE LISTING ( 1 ) GENERAL INFORMATION:

( i i i ) NUMBER OF SEQUENCES: 63

( 2 ) INFORMATION FOR SEQ ID NO:1:

( i ) SEQUENCE CHARACTERISTICS:

( A ) LENGTH: 1475 base pairs
        ( B ) TYPE: nucleic acid
        ( C ) STRANDEDNESS: single
        ( D ) TOPOLOGY: linear ( i x ) FEATURE:
    ( A ) NAME/KEY: CDS
    ( B ) LOCATION: 232..1416

( i x ) FEATURE:
    ( A ) NAME/KEY: mat_peptide
    ( B ) LOCATION: 232

( x i ) SEQUENCE DESCRIPTION: SEQ ID NO:1:

```
CCCTGTCAGT CTTAAGATTC TAGAAGTCGC TGTCCTATAC GGAACCCAAA ACTCTCACTG      60

TTAATGAAAT ACCATTGTCG GGGCGAAGAT GTAGCTCAGT GGTAAAATAC TTGCCAGCAC     120

ACACAAGAAT TAGACTTCAA CCGTCACCAA CTGCCCTGTG TAGGACGGTC GGTCACTGAA     180

AGAGAATATT GTCTGCAATA CTCTAATGAC ATCTGTCTGT GTTCATCTGA A ATG TTC     237
                                                        Met Phe
                                                          1

CAT TTA AAA CAC AGC AGC CTT ACT GTT GGA CCA TTT ATC TCA GTA ATG      285
His Leu Lys His Ser Ser Leu Thr Val Gly Pro Phe Ile Ser Val Met
         5              10                  15

ATT CTG CTC CGC TTT CTT TGT ACA GGA CGC AAC AAC AGT AAA GGA AGA      333
Ile Leu Leu Arg Phe Leu Cys Thr Gly Arg Asn Asn Ser Lys Gly Arg
     20              25                  30

AGT CTT ATT GGC AGA TTA GAA ACC CAG CCT CCA ATC ACT GGG AAA GGG      381
Ser Leu Ile Gly Arg Leu Glu Thr Gln Pro Pro Ile Thr Gly Lys Gly
 35              40                  45                      50

GTT CCG GTA GAA CCA GGC TTT TCC ATC GAT GAG TTC TCT GCG TCC ATC      429
Val Pro Val Glu Pro Gly Phe Ser Ile Asp Glu Phe Ser Ala Ser Ile
             55                  60                  65

CTC ACC GGG AAG CTG ACC ACG GTC TTT CTT CCG GTC GTC TAC ATT ATT      477
Leu Thr Gly Lys Leu Thr Thr Val Phe Leu Pro Val Val Tyr Ile Ile
         70                  75                  80

GTG TTT GTG ATT GGT TTG CCC AGT AAT GGC ATG GCC CTC TGG ATC TTC      525
Val Phe Val Ile Gly Leu Pro Ser Asn Gly Met Ala Leu Trp Ile Phe
     85                  90                  95

CTT TTC CGA ACG AAG AAG AAA CAC CCC GCC GTG ATT TAC ATG GCC AAC      573
Leu Phe Arg Thr Lys Lys Lys His Pro Ala Val Ile Tyr Met Ala Asn
 100                 105                 110

CTG GCC TTG GCC GAC CTC CTC TCT GTC ATC TGG TTC CCC CTG AAG ATC      621
Leu Ala Leu Ala Asp Leu Leu Ser Val Ile Trp Phe Pro Leu Lys Ile
115                 120                 125                 130

TCC TAC CAC CTA CAT GGC AAC AAC TGG GTC TAC GGG GAG GCC CTG TGC      669
Ser Tyr His Leu His Gly Asn Asn Trp Val Tyr Gly Glu Ala Leu Cys
                135                 140                 145

AAG GTG CTC ATT GGC TTT TTC TAT GGT AAC ATG TAT TGC TCC ATC CTC      717
Lys Val Leu Ile Gly Phe Phe Tyr Gly Asn Met Tyr Cys Ser Ile Leu
             150                 155                 160

TTC ATG ACC TGC CTC AGC GTG CAG AGG TAC TGG GTG ATC GTG AAC CCC      765
Phe Met Thr Cys Leu Ser Val Gln Arg Tyr Trp Val Ile Val Asn Pro
         165                 170                 175

ATG GGA CAC CCC AGG AAG AAG GCA AAC ATC GCC GTT GGC GTC TCC TTG      813
Met Gly His Pro Arg Lys Lys Ala Asn Ile Ala Val Gly Val Ser Leu
 180                 185                 190

GCA ATC TGG CTC CTG ATT TTT CTG GTC ACC ATC CCT TTG TAT GTC ATG      861
Ala Ile Trp Leu Leu Ile Phe Leu Val Thr Ile Pro Leu Tyr Val Met
195                 200                 205                 210

AAG CAG ACC ATC TAC ATT CCA GCA TTG AAC ATC ACC ACC TGT CAC GAT      909
Lys Gln Thr Ile Tyr Ile Pro Ala Leu Asn Ile Thr Thr Cys His Asp
                215                 220                 225

GTG CTG CCT GAG GAG GTA TTG GTG GGG GAC ATG TTC AAT TAC TTC CTC      957
Val Leu Pro Glu Glu Val Leu Val Gly Asp Met Phe Asn Tyr Phe Leu
             230                 235                 240
```

```
TCA CTG GCC ATT GGA GTC TTC CTG TTC CCG GCC CTC CTT ACT GCA TCT        1005
Ser Leu Ala Ile Gly Val Phe Leu Phe Pro Ala Leu Leu Thr Ala Ser
        245             250                 255

GCC TAC GTG CTC ATG ATC AAG ACG CTC CGC TCT TCT GCT ATG GAT GAA        1053
Ala Tyr Val Leu Met Ile Lys Thr Leu Arg Ser Ser Ala Met Asp Glu
        260             265                 270

CAC TCA GAG AAC AAA AGG CAG AGG GCT ATC CGA CTC ATC ATC ACC GTG        1101
His Ser Glu Asn Lys Arg Gln Arg Ala Ile Arg Leu Ile Ile Thr Val
275             280                 285                 290

CTG GCC ATG TAC TTC ATC TGC TTT GCT CCT AGC AAC CTT CTG CTC GTA        1149
Leu Ala Met Tyr Phe Ile Cys Phe Ala Pro Ser Asn Leu Leu Leu Val
        295             300                 305

GTG CAT TAT TTC CTA ATC AAA ACC CAG AGG CAG AGC CAC GTC TAC GCC        1197
Val His Tyr Phe Leu Ile Lys Thr Gln Arg Gln Ser His Val Tyr Ala
        310             315                 320

CTC TAC CTT GTC GCC CTC TGC CTG TCG ACC CTC AAC AGC TGC ATA GAC        1245
Leu Tyr Leu Val Ala Leu Cys Leu Ser Thr Leu Asn Ser Cys Ile Asp
        325             330                 335

CCC TTT GTC TAT TAC TTT GTC TCA AAA GAT TTC AGG GAT CAC GCC AGA        1293
Pro Phe Val Tyr Tyr Phe Val Ser Lys Asp Phe Arg Asp His Ala Arg
340             345                 350

AAC GCG CTC CTC TGC CGA AGT GTC CGC ACT GTG AAT CGC ATG CAA ATC        1341
Asn Ala Leu Leu Cys Arg Ser Val Arg Thr Val Asn Arg Met Gln Ile
355             360                 365                 370

TCG CTC AGC TCC AAC AAG TTC TCC AGG AAG TCC GGC TCC TAC TCT TCA        1389
Ser Leu Ser Ser Asn Lys Phe Ser Arg Lys Ser Gly Ser Tyr Ser Ser
                375             380                 385

AGC TCA ACC AGT GTT AAA ACC TCC TAC TGAGCTGTAC CTGAGGATGT              1436
Ser Ser Thr Ser Val Lys Thr Ser Tyr
        390             395

CAAGCCTGCT TGATGATGAT GATGATGATG GTGTGTGTG                             1475
```

( 2 ) INFORMATION FOR SEQ ID NO:2:

( i ) SEQUENCE CHARACTERISTICS:
( A ) LENGTH: 395 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Phe His Leu Lys His Ser Ser Leu Thr Val Gly Pro Phe Ile Ser
1               5                   10                  15

Val Met Ile Leu Leu Arg Phe Leu Cys Thr Gly Arg Asn Asn Ser Lys
            20                  25                  30

Gly Arg Ser Leu Ile Gly Arg Leu Glu Thr Gln Pro Pro Ile Thr Gly
        35                  40                  45

Lys Gly Val Pro Val Glu Pro Gly Phe Ser Ile Asp Glu Phe Ser Ala
    50                  55                  60

Ser Ile Leu Thr Gly Lys Leu Thr Thr Val Phe Leu Pro Val Val Tyr
65                  70                  75                  80

Ile Ile Val Phe Val Ile Gly Leu Pro Ser Asn Gly Met Ala Leu Trp
                85                  90                  95

Ile Phe Leu Phe Arg Thr Lys Lys Lys His Pro Ala Val Ile Tyr Met
            100                 105                 110

Ala Asn Leu Ala Leu Ala Asp Leu Leu Ser Val Ile Trp Phe Pro Leu
        115                 120                 125

Lys Ile Ser Tyr His Leu His Gly Asn Asn Trp Val Tyr Gly Glu Ala
```

| | | | | 130 | | | | | 135 | | | | | 140 | |
|---|---|---|---|---|---|---|---|---|---|---|---|---|---|---|---|
| Leu | Cys | Lys | Val | Leu | Ile | Gly | Phe | Phe | Tyr | Gly | Asn | Met | Tyr | Cys | Ser |
| 145 | | | | | 150 | | | | | 155 | | | | | 160 |
| Ile | Leu | Phe | Met | Thr | Cys | Leu | Ser | Val | Gln | Arg | Tyr | Trp | Val | Ile | Val |
| | | | | | 165 | | | | | 170 | | | | | 175 |
| Asn | Pro | Met | Gly | His | Pro | Arg | Lys | Lys | Ala | Asn | Ile | Ala | Val | Gly | Val |
| | | | | 180 | | | | | 185 | | | | | 190 | |
| Ser | Leu | Ala | Ile | Trp | Leu | Leu | Ile | Phe | Leu | Val | Thr | Ile | Pro | Leu | Tyr |
| | | | 195 | | | | | 200 | | | | | 205 | | |
| Val | Met | Lys | Gln | Thr | Ile | Tyr | Ile | Pro | Ala | Leu | Asn | Ile | Thr | Thr | Cys |
| | 210 | | | | | 215 | | | | | 220 | | | | |
| His | Asp | Val | Leu | Pro | Glu | Glu | Val | Leu | Val | Gly | Asp | Met | Phe | Asn | Tyr |
| 225 | | | | | 230 | | | | | 235 | | | | | 240 |
| Phe | Leu | Ser | Leu | Ala | Ile | Gly | Val | Phe | Leu | Phe | Pro | Ala | Leu | Leu | Thr |
| | | | | 245 | | | | | 250 | | | | | 255 | |
| Ala | Ser | Ala | Tyr | Val | Leu | Met | Ile | Lys | Thr | Leu | Arg | Ser | Ser | Ala | Met |
| | | | 260 | | | | | 265 | | | | | 270 | | |
| Asp | Glu | His | Ser | Glu | Asn | Lys | Arg | Gln | Arg | Ala | Ile | Arg | Leu | Ile | Ile |
| | | | 275 | | | | | 280 | | | | | 285 | | |
| Thr | Val | Leu | Ala | Met | Tyr | Phe | Ile | Cys | Phe | Ala | Pro | Ser | Asn | Leu | Leu |
| | 290 | | | | | 295 | | | | | 300 | | | | |
| Leu | Val | Val | His | Tyr | Phe | Leu | Ile | Lys | Thr | Gln | Arg | Gln | Ser | His | Val |
| 305 | | | | | 310 | | | | | 315 | | | | | 320 |
| Tyr | Ala | Leu | Tyr | Leu | Val | Ala | Leu | Cys | Leu | Ser | Thr | Leu | Asn | Ser | Cys |
| | | | | 325 | | | | | 330 | | | | | 335 | |
| Ile | Asp | Pro | Phe | Val | Tyr | Tyr | Phe | Val | Ser | Lys | Asp | Phe | Arg | Asp | His |
| | | | 340 | | | | | 345 | | | | | 350 | | |
| Ala | Arg | Asn | Ala | Leu | Leu | Cys | Arg | Ser | Val | Arg | Thr | Val | Asn | Arg | Met |
| | | 355 | | | | | 360 | | | | | 365 | | | |
| Gln | Ile | Ser | Leu | Ser | Ser | Asn | Lys | Phe | Ser | Arg | Lys | Ser | Gly | Ser | Tyr |
| | | 370 | | | | | 375 | | | | | 380 | | | |
| Ser | Ser | Ser | Ser | Thr | Ser | Val | Lys | Thr | Ser | Tyr | | | | | |
| 385 | | | | | 390 | | | | | 395 | | | | | |

( 2 ) INFORMATION FOR SEQ ID NO:3:

( i ) SEQUENCE CHARACTERISTICS:
        ( A ) LENGTH: 1255 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 56..1249

( i x ) FEATURE:
        ( A ) NAME/KEY: mat_peptide
        ( B ) LOCATION: 56

( x i ) SEQUENCE DESCRIPTION: SEQ ID NO:3:

```
CGCTCCAGGC CTGGGTGACA GCGAGACCCT GTCTCATAAA TTAAAAAATG AATAA ATG       58
                                                            Met
                                                             1

AAT GTA CTT TCA TTT GAA CAA ACC AGT GTT ACT GCT GAA ACA TTT ATT      106
Asn Val Leu Ser Phe Glu Gln Thr Ser Val Thr Ala Glu Thr Phe Ile
         5                  10                  15

TCT GTA ATG ACC CTT GTC TTC CTT TCT TGT ACA GGA ACC AAT AGA TCC      154
Ser Val Met Thr Leu Val Phe Leu Ser Cys Thr Gly Thr Asn Arg Ser
         20                  25                  30
```

```
TCT AAA GGA AGA AGC CTT ATT GGT AAG GTT GAT GGC ACA TCC CAC GTC        202
Ser Lys Gly Arg Ser Leu Ile Gly Lys Val Asp Gly Thr Ser His Val
    35              40              45

ACT GGA AAA GGA GTT ACA GTT GAA ACA GTC TTT TCT GTG GAT GAG TTT        250
Thr Gly Lys Gly Val Thr Val Glu Thr Val Phe Ser Val Asp Glu Phe
50              55              60              65

TCT GCA TCT GTC CTC ACT GGA AAA CTG ACC ACT GTC TTC CTT CCA ATT        298
Ser Ala Ser Val Leu Thr Gly Lys Leu Thr Thr Val Phe Leu Pro Ile
                70              75              80

GTC TAC ACA ATT GTG TTT GTG GTG GGT TTG CCA AGT AAC GGC ATG GCC        346
Val Tyr Thr Ile Val Phe Val Val Gly Leu Pro Ser Asn Gly Met Ala
            85              90              95

CTG TGG GTC TTT CTT TTC CGA ACT AAG AAG AAG CAC CCT GCT GTG ATT        394
Leu Trp Val Phe Leu Phe Arg Thr Lys Lys Lys His Pro Ala Val Ile
        100             105             110

TAC ATG GCC AAT CTG GCC TTG GCT GAC CTC CTC TCT GTC ATC TGG TTC        442
Tyr Met Ala Asn Leu Ala Leu Ala Asp Leu Leu Ser Val Ile Trp Phe
115             120             125

CCC TTG AAG ATT GCC TAT CAC ATA CAT GGC AAC AAC TGG ATT TAT GGG        490
Pro Leu Lys Ile Ala Tyr His Ile His Gly Asn Asn Trp Ile Tyr Gly
130             135             140             145

GAA GCT CTT TGT AAT GTG CTT ATT GGC TTT TTC TAT GGC AAC ATG TAC        538
Glu Ala Leu Cys Asn Val Leu Ile Gly Phe Phe Tyr Gly Asn Met Tyr
                150             155             160

TGT TCC ATT CTC TTC ATG ACC TGC CTC AGT GTG CAG AGG TAT TGG GTC        586
Cys Ser Ile Leu Phe Met Thr Cys Leu Ser Val Gln Arg Tyr Trp Val
            165             170             175

ATC GTG AAC CCC ATG GGG CAC TCC AGG AAG AAG GCA AAC ATT GCC ATT        634
Ile Val Asn Pro Met Gly His Ser Arg Lys Lys Ala Asn Ile Ala Ile
        180             185             190

GGC ATC TCC CTG GCA ATA TGG CTG CTG ATT CTG CTG GTC ACC ATC CCT        682
Gly Ile Ser Leu Ala Ile Trp Leu Leu Ile Leu Leu Val Thr Ile Pro
195             200             205

TTG TAT GTC GTG AAG CAG ACC ATC TTC ATT CCT GCC CTG AAC ATC ACG        730
Leu Tyr Val Val Lys Gln Thr Ile Phe Ile Pro Ala Leu Asn Ile Thr
210             215             220             225

ACC TGT CAT GAT GTT TTG CCT GAG CAG CTC TTG GTG GGA GAC ATG TTC        778
Thr Cys His Asp Val Leu Pro Glu Gln Leu Leu Val Gly Asp Met Phe
                230             235             240

AAT TAC TTC CTC TCT CTG GCC ATT GGG GTC TTT CTG TTC CCA GCC TTC        826
Asn Tyr Phe Leu Ser Leu Ala Ile Gly Val Phe Leu Phe Pro Ala Phe
            245             250             255

CTC ACA GCC TCT GCC TAT GTG CTG ATG ATC AGA ATG CTG CGA TCT TCT        874
Leu Thr Ala Ser Ala Tyr Val Leu Met Ile Arg Met Leu Arg Ser Ser
        260             265             270

GCC ATG GAT GAA AAC TCA GAG AAG AAA AGG AAG AGG GCC ATC AAA CTC        922
Ala Met Asp Glu Asn Ser Glu Lys Lys Arg Lys Arg Ala Ile Lys Leu
275             280             285

ATT GTC ACT GTC CTG GCC ATG TAC CTG ATC TGC TTC ACT CCT AGT AAC        970
Ile Val Thr Val Leu Ala Met Tyr Leu Ile Cys Phe Thr Pro Ser Asn
290             295             300             305

CTT CTG CTT GTG GTG CAT TAT TTT CTG ATT AAG AGC CAG GGC CAG AGC        1018
Leu Leu Leu Val Val His Tyr Phe Leu Ile Lys Ser Gln Gly Gln Ser
                310             315             320

CAT GTC TAT GCC CTG TAC ATT GTA GCC CTC TGC CTC TCT ACC CTT AAC        1066
His Val Tyr Ala Leu Tyr Ile Val Ala Leu Cys Leu Ser Thr Leu Asn
            325             330             335

AGC TGC ATC GAC CCC TTT GTC TAT TAC TTT GTT TCA CAT GAT TTC AGG        1114
Ser Cys Ile Asp Pro Phe Val Tyr Tyr Phe Val Ser His Asp Phe Arg
        340             345             350
```

```
GAT  CAT  GCA  AAG  AAC  GCT  CTC  CTT  TGC  CGA  AGT  GTC  CGC  ACT  GTA  AAG      1162
Asp  His  Ala  Lys  Asn  Ala  Leu  Leu  Cys  Arg  Ser  Val  Arg  Thr  Val  Lys
     355            360                      365

CAG  ATG  CAA  GTA  TCC  CTC  ACC  TCA  AAG  AAA  CAC  TCC  AGG  AAA  TCC  AGC      1210
Gln  Met  Gln  Val  Ser  Leu  Thr  Ser  Lys  Lys  His  Ser  Arg  Lys  Ser  Ser
370                      375                      380                      385

TCT  TAC  TCT  TCA  AGT  TCA  ACC  ACT  GTT  AAG  ACC  TCC  TAT  TGAGTT             1255
Ser  Tyr  Ser  Ser  Ser  Ser  Thr  Thr  Val  Lys  Thr  Ser  Tyr
               390                      395
```

( 2 ) INFORMATION FOR SEQ ID NO:4:

( i ) SEQUENCE CHARACTERISTICS:
        ( A ) LENGTH: 398 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Asn  Val  Leu  Ser  Phe  Glu  Gln  Thr  Ser  Val  Thr  Ala  Glu  Thr  Phe
1                   5                   10                      15

Ile  Ser  Val  Met  Thr  Leu  Val  Phe  Leu  Ser  Cys  Thr  Gly  Thr  Asn  Arg
               20                  25                      30

Ser  Ser  Lys  Gly  Arg  Ser  Leu  Ile  Gly  Lys  Val  Asp  Gly  Thr  Ser  His
          35                  40                      45

Val  Thr  Gly  Lys  Gly  Val  Thr  Val  Glu  Thr  Val  Phe  Ser  Val  Asp  Glu
     50                       55                      60

Phe  Ser  Ala  Ser  Val  Leu  Thr  Gly  Lys  Leu  Thr  Thr  Val  Phe  Leu  Pro
65                  70                      75                            80

Ile  Val  Tyr  Thr  Ile  Val  Phe  Val  Val  Gly  Leu  Pro  Ser  Asn  Gly  Met
               85                  90                                    95

Ala  Leu  Trp  Val  Phe  Leu  Phe  Arg  Thr  Lys  Lys  Lys  His  Pro  Ala  Val
               100                     105                     110

Ile  Tyr  Met  Ala  Asn  Leu  Ala  Leu  Ala  Asp  Leu  Leu  Ser  Val  Ile  Trp
          115                     120                     125

Phe  Pro  Leu  Lys  Ile  Ala  Tyr  His  Ile  His  Gly  Asn  Asn  Trp  Ile  Tyr
130                     135                     140

Gly  Glu  Ala  Leu  Cys  Asn  Val  Leu  Ile  Gly  Phe  Phe  Tyr  Gly  Asn  Met
145                     150                     155                     160

Tyr  Cys  Ser  Ile  Leu  Phe  Met  Thr  Cys  Leu  Ser  Val  Gln  Arg  Tyr  Trp
               165                     170                     175

Val  Ile  Val  Asn  Pro  Met  Gly  His  Ser  Arg  Lys  Lys  Ala  Asn  Ile  Ala
               180                     185                     190

Ile  Gly  Ile  Ser  Leu  Ala  Ile  Trp  Leu  Leu  Ile  Leu  Leu  Val  Thr  Ile
          195                     200                     205

Pro  Leu  Tyr  Val  Val  Lys  Gln  Thr  Ile  Phe  Ile  Pro  Ala  Leu  Asn  Ile
     210                     215                     220

Thr  Thr  Cys  His  Asp  Val  Leu  Pro  Glu  Gln  Leu  Leu  Val  Gly  Asp  Met
225                     230                     235                     240

Phe  Asn  Tyr  Phe  Leu  Ser  Leu  Ala  Ile  Gly  Val  Phe  Leu  Phe  Pro  Ala
               245                     250                     255

Phe  Leu  Thr  Ala  Ser  Ala  Tyr  Val  Leu  Met  Ile  Arg  Met  Leu  Arg  Ser
               260                     265                     270

Ser  Ala  Met  Asp  Glu  Asn  Ser  Glu  Lys  Lys  Arg  Lys  Arg  Ala  Ile  Lys
          275                     280                     285

Leu  Ile  Val  Thr  Val  Leu  Ala  Met  Tyr  Leu  Ile  Cys  Phe  Thr  Pro  Ser
```

|     |     |     |     | 290 |     |     |     |     | 295 |     |     |     |     | 300 |     |     |     |     |     |
| --- | --- | --- | --- | --- | --- | --- | --- | --- | --- | --- | --- | --- | --- | --- | --- | --- | --- | --- | --- |
| Asn | Leu | Leu | Leu | Val | Val | His | Tyr | Phe | Leu | Ile | Lys | Ser | Gln | Gly | Gln |
| 305 |     |     |     |     | 310 |     |     |     |     | 315 |     |     |     |     | 320 |
| Ser | His | Val | Tyr | Ala | Leu | Tyr | Ile | Val | Ala | Leu | Cys | Leu | Ser | Thr | Leu |
|     |     |     |     | 325 |     |     |     |     | 330 |     |     |     |     | 335 |     |
| Asn | Ser | Cys | Ile | Asp | Pro | Phe | Val | Tyr | Phe | Val | Ser | His | Asp | Phe |     |
|     |     |     | 340 |     |     |     |     | 345 |     |     |     | 350 |     |     |     |
| Arg | Asp | His | Ala | Lys | Asn | Ala | Leu | Leu | Cys | Arg | Ser | Val | Arg | Thr | Val |
|     |     | 355 |     |     |     |     | 360 |     |     |     |     | 365 |     |     |     |
| Lys | Gln | Met | Gln | Val | Ser | Leu | Thr | Ser | Lys | Lys | His | Ser | Arg | Lys | Ser |
|     | 370 |     |     |     |     | 375 |     |     |     |     | 380 |     |     |     |     |
| Ser | Ser | Tyr | Ser | Ser | Ser | Ser | Thr | Thr | Val | Lys | Thr | Ser | Tyr |     |     |
| 385 |     |     |     |     | 390 |     |     |     |     | 395 |     |     |     |     |     |

( 2 ) INFORMATION FOR SEQ ID NO:5:

( i ) SEQUENCE CHARACTERISTICS:
( A ) LENGTH: 395 amino acids
( B ) TYPE: amino acid
( C ) STRANDEDNESS: single
( D ) TOPOLOGY: linear ( x i ) SEQUENCE DESCRIPTION: SEQ ID NO:5:

|     |     |     |     |     |     |     |     |     |     |     |     |     |     |     |
| --- | --- | --- | --- | --- | --- | --- | --- | --- | --- | --- | --- | --- | --- | --- |
| Met | Phe | His | Leu | Lys | His | Ser | Ser | Leu | Thr | Val | Gly | Pro | Phe | Ile | Ser |
| 1   |     |     |     | 5   |     |     |     |     | 10  |     |     |     |     | 15  |     |
| Val | Met | Ile | Leu | Leu | Arg | Phe | Leu | Cys | Thr | Gly | Arg | Asn | Asn | Ser | Lys |
|     |     |     | 20  |     |     |     |     | 25  |     |     |     |     | 30  |     |     |
| Gly | Arg | Ser | Leu | Ile | Gly | Arg | Leu | Glu | Thr | Gln | Pro | Pro | Ile | Thr | Gly |
|     |     | 35  |     |     |     |     | 40  |     |     |     |     | 45  |     |     |     |
| Lys | Gly | Val | Pro | Val | Glu | Pro | Gly | Phe | Ser | Ile | Asp | Glu | Phe | Ser | Ala |
|     | 50  |     |     |     |     | 55  |     |     |     |     | 60  |     |     |     |     |
| Ser | Ile | Leu | Thr | Gly | Lys | Leu | Thr | Thr | Val | Phe | Leu | Pro | Val | Val | Tyr |
| 65  |     |     |     |     | 70  |     |     |     |     | 75  |     |     |     |     | 80  |
| Ile | Ile | Val | Phe | Val | Ile | Gly | Leu | Pro | Ser | Asn | Gly | Met | Ala | Leu | Trp |
|     |     |     |     | 85  |     |     |     |     | 90  |     |     |     |     | 95  |     |
| Ile | Phe | Leu | Phe | Arg | Thr | Lys | Lys | Lys | His | Pro | Ala | Val | Ile | Tyr | Met |
|     |     |     |     | 100 |     |     |     |     | 105 |     |     |     |     | 110 |     |
| Ala | Asn | Leu | Ala | Leu | Ala | Asp | Leu | Leu | Ser | Val | Ile | Trp | Phe | Pro | Leu |
|     |     | 115 |     |     |     |     | 120 |     |     |     |     | 125 |     |     |     |
| Lys | Ile | Ser | Tyr | His | Leu | His | Gly | Asn | Asn | Trp | Val | Tyr | Gly | Glu | Ala |
|     | 130 |     |     |     |     | 135 |     |     |     |     | 140 |     |     |     |     |
| Leu | Cys | Lys | Val | Leu | Ile | Gly | Phe | Phe | Tyr | Gly | Asn | Met | Tyr | Cys | Ser |
| 145 |     |     |     |     | 150 |     |     |     |     | 155 |     |     |     |     | 160 |
| Ile | Leu | Phe | Met | Thr | Cys | Leu | Ser | Val | Gln | Arg | Tyr | Trp | Val | Ile | Val |
|     |     |     |     | 165 |     |     |     |     | 170 |     |     |     |     | 175 |     |
| Asn | Pro | Met | Gly | His | Pro | Arg | Lys | Lys | Ala | Asn | Ile | Ala | Val | Gly | Val |
|     |     |     | 180 |     |     |     |     | 185 |     |     |     |     | 190 |     |     |
| Ser | Leu | Ala | Ile | Trp | Leu | Leu | Ile | Phe | Leu | Val | Thr | Ile | Pro | Leu | Tyr |
|     |     | 195 |     |     |     |     | 200 |     |     |     |     | 205 |     |     |     |
| Val | Met | Lys | Gln | Thr | Ile | Tyr | Ile | Pro | Ala | Leu | Asn | Ile | Thr | Thr | Cys |
|     | 210 |     |     |     |     | 215 |     |     |     |     | 220 |     |     |     |     |
| His | Asp | Val | Leu | Pro | Glu | Glu | Val | Leu | Val | Gly | Asp | Met | Phe | Asn | Tyr |
| 225 |     |     |     |     | 230 |     |     |     |     | 235 |     |     |     |     | 240 |
| Phe | Leu | Ser | Leu | Ala | Ile | Gly | Val | Phe | Leu | Phe | Pro | Ala | Leu | Leu | Thr |
|     |     |     |     | 245 |     |     |     |     | 250 |     |     |     |     | 255 |     |
| Ala | Ser | Ala | Tyr | Val | Leu | Met | Ile | Lys | Thr | Leu | Arg | Ser | Ser | Ala | Met |

-continued

```
                          260                        265                         270
       Asp  Glu  His  Ser  Glu  Lys  Lys  Arg  Gln  Arg  Ala  Ile  Arg  Leu  Ile  Ile
                 275                      280                      285

Thr  Val  Leu  Ala  Met  Tyr  Phe  Ile  Cys  Phe  Ala  Pro  Ser  Asn  Leu  Leu
            290                      295                      300

Leu  Val  Val  His  Tyr  Phe  Leu  Ile  Lys  Thr  Gln  Arg  Gln  Ser  His  Val
       305                      310                      315                      320

Tyr  Ala  Leu  Tyr  Leu  Val  Ala  Leu  Cys  Leu  Ser  Thr  Leu  Asn  Ser  Cys
                           325                      330                      335

Ile  Asp  Pro  Phe  Val  Tyr  Tyr  Phe  Val  Ser  Lys  Asp  Phe  Arg  Asp  His
                      340                      345                      350

Ala  Arg  Asn  Ala  Leu  Leu  Cys  Arg  Ser  Val  Arg  Thr  Val  Asn  Arg  Met
                 355                      360                      365

Gln  Ile  Ser  Leu  Ser  Ser  Asn  Lys  Phe  Ser  Arg  Lys  Ser  Cys  Ser  Tyr
            370                      375                      380

Ser  Ser  Ser  Ser  Thr  Ser  Val  Lys  Thr  Ser  Tyr
       385                      390                      395
```

( 2 ) INFORMATION FOR SEQ ID NO:6:

( i ) SEQUENCE CHARACTERISTICS:
        ( A ) LENGTH: 398 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
       Met  Asn  Val  Leu  Ser  Phe  Glu  Gln  Thr  Ser  Val  Thr  Ala  Glu  Thr  Phe
       1                   5                        10                       15

Ile  Ser  Val  Met  Ile  Leu  Val  Phe  Leu  Ser  Cys  Thr  Gly  Thr  Asn  Arg
                      20                       25                       30

Ser  Ser  Lys  Gly  Arg  Ser  Leu  Ile  Gly  Lys  Val  Asp  Gly  Thr  Ser  His
                 35                       40                       45

Val  Thr  Gly  Lys  Gly  Val  Ile  Val  Glu  Ile  Val  Phe  Ser  Val  Asp  Glu
            50                       55                       60

Phe  Ser  Ala  Ser  Val  Leu  Thr  Gly  Lys  Leu  Thr  Thr  Val  Phe  Leu  Pro
       65                       70                       75                       80

Ile  Val  Tyr  Ile  Ile  Val  Phe  Val  Val  Gly  Leu  Pro  Ser  Asn  Gly  Met
                           85                       90                       95

Ala  Leu  Trp  Val  Phe  Leu  Phe  Arg  Thr  Lys  Lys  Lys  His  Pro  Ala  Val
                      100                      105                      110

Ile  Tyr  Met  Ala  Asn  Leu  Ala  Leu  Ala  Asp  Leu  Leu  Ser  Val  Ile  Trp
                 115                      120                      125

Phe  Pro  Leu  Lys  Ile  Ala  Tyr  His  Ile  His  Gly  Asn  Asn  Trp  Ile  Tyr
            130                      135                      140

Gly  Glu  Ala  Leu  Cys  Asn  Val  Leu  Ile  Gly  Phe  Phe  Tyr  Gly  Asn  Met
       145                      150                      155                      160

Tyr  Cys  Ser  Ile  Leu  Phe  Met  Thr  Cys  Leu  Ser  Val  Gln  Arg  Tyr  Trp
                           165                      170                      175

Val  Ile  Val  Asn  Pro  Met  Gly  His  Ser  Arg  Lys  Lys  Ala  Asn  Ile  Ala
                      180                      185                      190

Ile  Gly  Ile  Ser  Leu  Ala  Ile  Trp  Leu  Leu  Ile  Leu  Leu  Val  Thr  Ile
                 195                      200                      205

Pro  Leu  Tyr  Val  Val  Lys  Gln  Thr  Ile  Phe  Ile  Pro  Ala  Leu  Asn  Ile
            210                      215                      220

Thr  Thr  Cys  His  Asp  Val  Leu  Pro  Glu  Gln  Val  Leu  Val  Gly  Asp  Met
```

```
                    225                      230                      235                      240
          Phe  Asn  Tyr  Phe  Leu  Ser  Leu  Ala  Ile  Gly  Val  Phe  Leu  Phe  Pro  Ala
                              245                      250                      255

Phe  Leu  Thr  Ala  Ser  Ala  Tyr  Val  Leu  Met  Ile  Arg  Met  Leu  Arg  Ser
                              260                      265                      270

Ser  Ala  Met  Asp  Glu  Asn  Ser  Glu  Lys  Lys  Arg  Lys  Arg  Ala  Ile  Lys
                         275                      280                      285

Leu  Ile  Val  Thr  Val  Leu  Ala  Met  Tyr  Leu  Ile  Cys  Phe  Ile  Pro  Ser
                    290                      295                      300

Asn  Leu  Leu  Leu  Val  Val  His  Tyr  Phe  Leu  Ile  Lys  Ser  Gln  Gly  Gln
          305                      310                      315                      320

Ser  His  Val  Tyr  Ala  Leu  Tyr  Ile  Val  Ala  Leu  Cys  Leu  Ser  Thr  Leu
                              325                      330                      335

Asn  Ser  Cys  Ile  Asp  Pro  Phe  Val  Tyr  Tyr  Phe  Val  Ser  His  Asp  Phe
                              340                      345                      350

Arg  Asp  His  Ala  Lys  Asn  Ala  Leu  Leu  Cys  Arg  Ser  Val  Arg  Thr  Val
                         355                      360                      365

Lys  Gln  Met  Gln  Val  Ser  Leu  Ile  Ser  Lys  Lys  His  Ser  Arg  Lys  Ser
                    370                      375                      380

Ser  Ser  Tyr  Ser  Ser  Ser  Ser  Thr  Ile  Val  Lys  Thr  Ser  Tyr
          385                      390                      395
```

( 2 ) INFORMATION FOR SEQ ID NO:7:

( i ) SEQUENCE CHARACTERISTICS:
        ( A ) LENGTH: 425 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
          Met  Gly  Pro  Arg  Arg  Leu  Leu  Leu  Val  Ala  Ala  Cys  Phe  Ser  Leu  Cys
          1                   5                        10                       15

Gly  Phe  Leu  Leu  Ser  Ala  Arg  Thr  Arg  Ala  Arg  Arg  Pro  Glu  Ser  Lys
                              20                       25                       30

Ala  Thr  Asn  Ala  Thr  Leu  Asp  Pro  Arg  Ser  Phe  Leu  Leu  Arg  Asn  Pro
                         35                       40                       45

Asn  Asp  Lys  Tyr  Glu  Pro  Phe  Trp  Glu  Asp  Glu  Lys  Asn  Glu  Ser
                    50                       55                       60

Gly  Leu  Thr  Glu  Tyr  Arg  Leu  Val  Ser  Ile  Asn  Lys  Ser  Ser  Pro  Leu
          65                       70                       75                       80

Gln  Lys  Gln  Leu  Pro  Ala  Phe  Ile  Ser  Glu  Asp  Ala  Ser  Gly  Tyr  Leu
                              85                       90                       95

Thr  Ser  Ser  Trp  Leu  Thr  Leu  Phe  Val  Pro  Ser  Val  Tyr  Thr  Gly  Val
                              100                      105                      110

Phe  Val  Val  Ser  Leu  Pro  Leu  Asn  Ile  Met  Ala  Ile  Val  Val  Phe  Ile
                         115                      120                      125

Leu  Lys  Met  Lys  Val  Lys  Lys  Pro  Ala  Val  Val  Tyr  Met  Leu  His  Leu
                    130                      135                      140

Ala  Thr  Ala  Asp  Val  Leu  Phe  Val  Ser  Val  Leu  Pro  Phe  Lys  Ile  Ser
          145                      150                      155                      160

Tyr  Tyr  Phe  Ser  Gly  Ser  Asp  Trp  Gln  Phe  Gly  Ser  Glu  Leu  Cys  Arg
                              165                      170                      175

Phe  Val  Thr  Ala  Ala  Phe  Tyr  Cys  Asn  Met  Tyr  Ala  Ser  Ile  Leu  Leu
                         180                      185                      190

Met  Thr  Val  Ile  Ser  Ile  Asp  Arg  Phe  Leu  Ala  Val  Val  Tyr  Pro  Met
```

-continued

```
            195                        200                        205
    Gln  Ser  Leu  Ser  Trp  Arg  Thr  Leu  Gly  Arg  Ala  Ser  Phe  Thr  Cys  Leu
         210                      215                      220
    Ala  Ile  Trp  Ala  Leu  Ala  Ile  Ala  Gly  Val  Val  Pro  Leu  Val  Leu  Lys
    225                      230                      235                      240
    Glu  Gln  Thr  Ile  Gln  Val  Pro  Gly  Leu  Asn  Ile  Thr  Thr  Cys  His  Asp
                        245                      250                           255
    Val  Leu  Asn  Glu  Thr  Leu  Leu  Glu  Gly  Tyr  Tyr  Ala  Tyr  Tyr  Phe  Ser
                   260                      265                      270
    Ala  Phe  Ser  Ala  Val  Phe  Phe  Val  Pro  Leu  Ile  Ile  Ser  Thr  Val
              275                      280                      285
    Cys  Tyr  Val  Ser  Ile  Ile  Arg  Cys  Leu  Ser  Ser  Ser  Ala  Val  Ala  Asn
         290                      295                      300
    Arg  Ser  Lys  Lys  Ser  Arg  Ala  Leu  Phe  Leu  Ser  Ala  Ala  Val  Phe  Cys
    305                      310                      315                      320
    Ile  Phe  Ile  Ile  Cys  Phe  Gly  Pro  Thr  Asn  Val  Leu  Leu  Ile  Ala  His
                        325                      330                      335
    Tyr  Ser  Phe  Leu  Ser  His  Thr  Ser  Thr  Thr  Glu  Ala  Ala  Tyr  Phe  Ala
                   340                      345                      350
    Tyr  Leu  Leu  Cys  Val  Cys  Val  Ser  Ser  Ile  Ser  Ser  Cys  Ile  Asp  Pro
                   355                      360                      365
    Leu  Ile  Tyr  Tyr  Tyr  Ala  Ser  Ser  Glu  Cys  Gln  Arg  Tyr  Val  Tyr  Ser
         370                      375                      380
    Ile  Leu  Cys  Cys  Lys  Glu  Ser  Ser  Asp  Pro  Ser  Ser  Tyr  Asn  Ser  Ser
    385                      390                      395                      400
    Gly  Gln  Leu  Met  Ala  Ser  Lys  Met  Asp  Thr  Cys  Ser  Ser  Asn  Leu  Asn
                        405                      410                      415
    Asn  Ser  Ile  Tyr  Lys  Lys  Leu  Leu  Thr
                   420                      425
```

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

```
    Arg  Asn  Asn  Ser  Lys  Gly  Arg
    1                   5
```

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note="This position is Mpr =
            3- mercaptopropionic acid."

( x i ) SEQUENCE DESCRIPTION: SEQ ID NO:9:

```
    Xaa  Leu  Leu  Gly  Lys
    1                   5
```

( 2 ) INFORMATION FOR SEQ ID NO:10:

(i) SEQUENCE CHARACTERISTICS:
   (A) LENGTH: 5 amino acids
   (B) TYPE: amino acid
   (C) STRANDEDNESS: single
   (D) TOPOLOGY: linear (ix) FEATURE:
   (A) NAME/KEY: Modified-site
   (B) LOCATION: 1
   (D) OTHER INFORMATION: /note="This position is Mpr = 3- mercaptopropionic acid."

(xi) SEQUENCE DESCRIPTION: SEQ ID NO:10:

Xaa Leu Ile Gly Arg
1               5

(2) INFORMATION FOR SEQ ID NO:11:

(i) SEQUENCE CHARACTERISTICS:
   (A) LENGTH: 5 amino acids
   (B) TYPE: amino acid
   (C) STRANDEDNESS: single
   (D) TOPOLOGY: linear (ix) FEATURE:
   (A) NAME/KEY: Modified-site
   (B) LOCATION: 1
   (D) OTHER INFORMATION: /note="This position is Mpr = 3- mercaptopropionic acid."

(ix) FEATURE:
   (A) NAME/KEY: Modified-site
   (B) LOCATION: 2
   (D) OTHER INFORMATION: /note="This position is Cha = cyclohexylalanine."

(xi) SEQUENCE DESCRIPTION: SEQ ID NO:11:

Xaa Xaa Leu Lys Gly
1               5

(2) INFORMATION FOR SEQ ID NO:12:

(i) SEQUENCE CHARACTERISTICS:
   (A) LENGTH: 5 amino acids
   (B) TYPE: amino acid
   (C) STRANDEDNESS: single
   (D) TOPOLOGY: linear (ix) FEATURE:
   (A) NAME/KEY: Modified-site
   (B) LOCATION: 1
   (D) OTHER INFORMATION: /note="This position is Mpr = 3- mercaptopropionic acid."

(ix) FEATURE:
   (A) NAME/KEY: Modified-site
   (B) LOCATION: 2
   (D) OTHER INFORMATION: /note="This position is (Cha) = cyclohexylalanine."

(xi) SEQUENCE DESCRIPTION: SEQ ID NO:12:

Xaa Xaa Ile Gly Arg
1               5

(2) INFORMATION FOR SEQ ID NO:13:

(i) SEQUENCE CHARACTERISTICS:
   (A) LENGTH: 6 amino acids
   (B) TYPE: amino acid
   (C) STRANDEDNESS: single
   (D) TOPOLOGY: linear (ix) FEATURE:

( A ) NAME/KEY: Modified-site
                    ( B ) LOCATION: 1
                    ( D ) OTHER INFORMATION: /note="This position is Mpr =
                          3- mercaptopropionic acid."

( x i ) SEQUENCE DESCRIPTION: SEQ ID NO:13:

Xaa  Leu  Leu  Gly  Lys  Lys
        1                      5

( 2 ) INFORMATION FOR SEQ ID NO:14:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: linear ( i x ) FEATURE:
                    ( A ) NAME/KEY: Modified-site
                    ( B ) LOCATION: 1
                    ( D ) OTHER INFORMATION: /note="This position is Mpr =
                          3- mercaptopropionic acid."

( x i ) SEQUENCE DESCRIPTION: SEQ ID NO:14:

Xaa  Leu  Ile  Gly  Arg  Lys
        1                      5

( 2 ) INFORMATION FOR SEQ ID NO:15:

( i ) SEQUENCE CHARACTERISTICS:
                    ( A ) LENGTH: 10 amino acids
                    ( B ) TYPE: amino acid
                    ( C ) STRANDEDNESS: single
                    ( D ) TOPOLOGY: linear ( i x ) FEATURE:
                    ( A ) NAME/KEY: Modified-site
                    ( B ) LOCATION: 1
                    ( D ) OTHER INFORMATION: /note="This position is Mpr =
                          3- mercaptopropionic acid."

( x i ) SEQUENCE DESCRIPTION: SEQ ID NO:15:

Xaa  Leu  Ile  Gly  Arg  Lys  Glu  Thr  Gln  Pro
        1                      5                        10

( 2 ) INFORMATION FOR SEQ ID NO:16:

( i ) SEQUENCE CHARACTERISTICS:
                    ( A ) LENGTH: 10 amino acids
                    ( B ) TYPE: amino acid
                    ( C ) STRANDEDNESS: single
                    ( D ) TOPOLOGY: linear ( i x ) FEATURE:
                    ( A ) NAME/KEY: Modified-site
                    ( B ) LOCATION: 1
                    ( D ) OTHER INFORMATION: /note="This position is Mpr =
                          3- mercaptopropionic acid."

( x i ) SEQUENCE DESCRIPTION: SEQ ID NO:16:

Xaa  Leu  Leu  Gly  Lys  Lys  Asp  Gly  Thr  Ser
        1                      5                        10

( 2 ) INFORMATION FOR SEQ ID NO:17:

( i ) SEQUENCE CHARACTERISTICS:
                    ( A ) LENGTH: 5 amino acids
                    ( B ) TYPE: amino acid
                    ( C ) STRANDEDNESS: single
                    ( D ) TOPOLOGY: linear ( i x ) FEATURE:

(A) NAME/KEY: Modified-site
(B) LOCATION: 1
(D) OTHER INFORMATION: /note="This position is
(n-pentyl)2-N-Leu."

(xi) SEQUENCE DESCRIPTION: SEQ ID NO:17:

Xaa Ile Gly Arg Lys
1               5

(2) INFORMATION FOR SEQ ID NO:18:

(i) SEQUENCE CHARACTERISTICS:
    (A) LENGTH: 6 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /note="This position is
    (Me-N-(n-pentyl)."

(xi) SEQUENCE DESCRIPTION: SEQ ID NO:18:

Xaa Leu Ile Gly Arg Lys
1                   5

(2) INFORMATION FOR SEQ ID NO:19:

(i) SEQUENCE CHARACTERISTICS:
    (A) LENGTH: 12 amino acids
    (B) TYPE: amino acid
    (C) STRANDEDNESS: single
    (D) TOPOLOGY: linear (xi) SEQUENCE DESCRIPTION: SEQ ID NO:19:

Ser Lys Gly Arg Ser Leu Ile Gly Arg Leu Glu Thr
1               5                   10

(2) INFORMATION FOR SEQ ID NO:20:

(i) SEQUENCE CHARACTERISTICS:
    (A) LENGTH: 17 amino acids
    (B) TYPE: amino acid
    (C) STRANDEDNESS: single
    (D) TOPOLOGY: linear (xi) SEQUENCE DESCRIPTION: SEQ ID NO:20:

Ile Ser Tyr His Leu His Gly Asn Asn Trp Val Tyr Gly Glu Ala Leu
1               5                   10                  15

Cys (2) INFORMATION FOR SEQ ID NO:21:

(i) SEQUENCE CHARACTERISTICS:
    (A) LENGTH: 31 amino acids
    (B) TYPE: amino acid
    (C) STRANDEDNESS: single
    (D) TOPOLOGY: linear (xi) SEQUENCE DESCRIPTION: SEQ ID NO:21:

Gln Thr Ile Tyr Ile Pro Ala Leu Asn Ile Thr Thr Cys His Asp Val
1               5                   10                  15

Leu Pro Glu Glu Val Leu Val Gly Asp Met Phe Asn Tyr Phe Leu
                20                  25                  30

(2) INFORMATION FOR SEQ ID NO:22:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( x i ) SEQUENCE DESCRIPTION: SEQ ID NO:22:

```
His Tyr Phe Leu Ile Lys Thr Gln Arg Gln Ser His Val Tyr Ala
1               5                   10                  15
```

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:23:

```
Ser Leu Ile Gly Arg Leu
1               5
```

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:24:

```
Ser Leu Ile Gly Arg Ala
1               5
```

( 2 ) INFORMATION FOR SEQ ID NO:25:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:25:

```
Ser Leu Ile Gly Ala Leu
1               5
```

( 2 ) INFORMATION FOR SEQ ID NO:26:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:26:

```
Ser Leu Ile Ala Arg Leu
1               5
```

( 2 ) INFORMATION FOR SEQ ID NO:27:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:27:

```
Ser Leu Ala Gly Arg Leu
1               5
```

( 2 ) INFORMATION FOR SEQ ID NO:28:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:28:

```
Ser Ala Ile Gly Arg Leu
 1               5
```

( 2 ) INFORMATION FOR SEQ ID NO:29:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:29:

```
Ala Leu Ile Gly Arg Leu
 1               5
```

( 2 ) INFORMATION FOR SEQ ID NO:30:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:30:

```
Ser Phe Phe Leu Arg Trp
 1               5
```

( 2 ) INFORMATION FOR SEQ ID NO:31:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:31:

```
Arg Asn Asn Ser Ser Lys Gly Arg
 1               5
```

( 2 ) INFORMATION FOR SEQ ID NO:32:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( x i ) SEQUENCE DESCRIPTION: SEQ ID NO:32:

```
Ser Leu Ile Gly Arg Leu Glu Thr Gln Pro Pro Ile Thr
 1               5                   10
```

( 2 ) INFORMATION FOR SEQ ID NO:33:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:33:

```
Ser Leu Ile Gly Arg Leu Glu Thr Gln Pro Pro Ile
1               5                   10
```

( 2 ) INFORMATION FOR SEQ ID NO:34:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:34:

```
Ser Leu Ile Gly Arg Leu Glu Thr Gln Pro Pro
1               5                   10
```

( 2 ) INFORMATION FOR SEQ ID NO:35:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:35:

```
Ser Leu Ile Gly Arg Leu Glu Thr Gln Pro
1               5                   10
```

( 2 ) INFORMATION FOR SEQ ID NO:36:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:36:

```
Ser Leu Ile Gly Arg Leu Glu Thr Gln
1               5
```

( 2 ) INFORMATION FOR SEQ ID NO:37:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:37:

```
Ser Leu Ile Gly Arg Leu Glu Thr
1               5
```

( 2 ) INFORMATION FOR SEQ ID NO:38:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:38:

```
Ser Leu Ile Gly Arg Leu Glu
1               5
```

( 2 ) INFORMATION FOR SEQ ID NO:39:

( i ) SEQUENCE CHARACTERISTICS:
        ( A ) LENGTH: 6 amino acids (B) TYPE: amino acid
(C) STRANDEDNESS: single
(D) TOPOLOGY: linear (xi) SEQUENCE DESCRIPTION: SEQ ID NO:39:

Ser Leu Ile Gly Arg Leu
1               5

(2) INFORMATION FOR SEQ ID NO:40:

(i) SEQUENCE CHARACTERISTICS:
    (A) LENGTH: 5 amino acids
    (B) TYPE: amino acid
    (C) STRANDEDNESS: single
    (D) TOPOLOGY: linear (xi) SEQUENCE DESCRIPTION: SEQ ID NO:40:

Ser Leu Ile Gly Arg
1               5

(2) INFORMATION FOR SEQ ID NO:41:

(i) SEQUENCE CHARACTERISTICS:
    (A) LENGTH: 13 amino acids
    (B) TYPE: amino acid
    (C) STRANDEDNESS: single
    (D) TOPOLOGY: linear (xi) SEQUENCE DESCRIPTION: SEQ ID NO:41:

Ser Leu Leu Gly Lys Val Asp Gly Thr Ser His Val Thr
1               5                   10

(2) INFORMATION FOR SEQ ID NO:42:

(i) SEQUENCE CHARACTERISTICS:
    (A) LENGTH: 12 amino acids
    (B) TYPE: amino acid
    (C) STRANDEDNESS: single
    (D) TOPOLOGY: linear (xi) SEQUENCE DESCRIPTION: SEQ ID NO:42:

Ser Leu Leu Gly Lys Val Asp Gly Thr Ser His Val
1               5                   10

(2) INFORMATION FOR SEQ ID NO:43:

(i) SEQUENCE CHARACTERISTICS:
    (A) LENGTH: 11 amino acids
    (B) TYPE: amino acid
    (C) STRANDEDNESS: single
    (D) TOPOLOGY: linear (xi) SEQUENCE DESCRIPTION: SEQ ID NO:43:

Ser Leu Leu Gly Lys Val Asp Gly Thr Ser His
1               5                   10

(2) INFORMATION FOR SEQ ID NO:44:

(i) SEQUENCE CHARACTERISTICS:
    (A) LENGTH: 10 amino acids
    (B) TYPE: amino acid
    (C) STRANDEDNESS: single
    (D) TOPOLOGY: linear (xi) SEQUENCE DESCRIPTION: SEQ ID NO:44:

Ser Leu Leu Gly Lys Val Asp Gly Thr Ser
1               5                   10

(2) INFORMATION FOR SEQ ID NO:45:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:45:

Ser  Leu  Leu  Gly  Lys  Val  Asp  Gly  Thr
    1                      5

(2) INFORMATION FOR SEQ ID NO:46:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:46:

Ser  Leu  Leu  Gly  Lys  Val  Asp  Gly
    1                      5

(2) INFORMATION FOR SEQ ID NO:47:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:47:

Ser  Leu  Leu  Gly  Lys  Val  Asp
    1                      5

(2) INFORMATION FOR SEQ ID NO:48:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:48:

Ser  Leu  Leu  Gly  Lys  Val
    1                      5

(2) INFORMATION FOR SEQ ID NO:49:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:49:

Ser  Leu  Leu  Gly  Lys
    1                      5

(2) INFORMATION FOR SEQ ID NO:50:

(i) SEQUENCE CHARACTERISTICS:
        (A) LENGTH: 5 amino acids
        (B) TYPE: amino acid
        (C) STRANDEDNESS: single
        (D) TOPOLOGY: linear (ix) FEATURE:
        (A) NAME/KEY: Modified-site ( B ) LOCATION: 2
( D ) OTHER INFORMATION: /note="This position is (Cha) = cyclohexylalanine."

( x i ) SEQUENCE DESCRIPTION: SEQ ID NO:50:

Ser Xaa Ile Gly Arg
1               5

( 2 ) INFORMATION FOR SEQ ID NO:51:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 2
( D ) OTHER INFORMATION: /note="This position is (Cha) = cyclohexylalanine."

( x i ) SEQUENCE DESCRIPTION: SEQ ID NO:51:

Ser Xaa Leu Gly Lys
1               5

( 2 ) INFORMATION FOR SEQ ID NO:52:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note="This position is (2,3-diaP) = 2,3-diamino propionic."

( x i ) SEQUENCE DESCRIPTION: SEQ ID NO:52:

Xaa Ile Gly Arg
1

( 2 ) INFORMATION FOR SEQ ID NO:53:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note="This position is (2,3-diaP) = 2,3-diamino propionic."

( x i ) SEQUENCE DESCRIPTION: SEQ ID NO:53:

Xaa Leu Leu Gly Lys
1               5

( 2 ) INFORMATION FOR SEQ ID NO:54:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( x i ) SEQUENCE DESCRIPTION: SEQ ID NO:54:

```
Ser  Leu  Leu  Gly  Lys  Arg
1                 5
```

( 2 ) INFORMATION FOR SEQ ID NO:55:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:55:

```
Ser  Leu  Ile  Gly  Arg  Arg
1                 5
```

( 2 ) INFORMATION FOR SEQ ID NO:56:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 2
        ( D ) OTHER INFORMATION: /note="This position is (Cha) =
            cyclohexylalanine."

( x i ) SEQUENCE DESCRIPTION: SEQ ID NO:56:

```
Ser  Xaa  Leu  Gly  Lys  Lys
1                 5
```

( 2 ) INFORMATION FOR SEQ ID NO:57:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 2
        ( D ) OTHER INFORMATION: /note="This position is (Cha) =
            cyclohexylalanine."

( x i ) SEQUENCE DESCRIPTION: SEQ ID NO:57:

```
Ser  Xaa  Ile  Gly  Arg  Lys
1                 5
```

( 2 ) INFORMATION FOR SEQ ID NO:58:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note="This position is (2,3-diaP)
            = 2,3-diamino propionic."

( x i ) SEQUENCE DESCRIPTION: SEQ ID NO:58:

```
Xaa  Leu  Ile  Gly  Arg  Lys
1                 5
```

( 2 ) INFORMATION FOR SEQ ID NO:59:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note="This position is (2,3-diaP)
        = 2,3-diamino propionic."

( x i ) SEQUENCE DESCRIPTION: SEQ ID NO:59:

```
Xaa  Leu  Leu  Gly  Lys  Lys
 1                 5
```

( 2 ) INFORMATION FOR SEQ ID NO:60:

( i ) SEQUENCE CHARACTERISTICS:
    ( A ) LENGTH: 2732 base pairs
    ( B ) TYPE: nucleic acid
    ( C ) STRANDEDNESS: single
    ( D ) TOPOLOGY: linear ( i x ) FEATURE:
    ( A ) NAME/KEY: CDS
    ( B ) LOCATION: 73..1269

( x i ) SEQUENCE DESCRIPTION: SEQ ID NO:60:

```
CCCTGTGCTC AGAGTAGGGC TCCGAGTTTC GAACCACTGG TGGCGGATTG CCCGCCCGCC         60

CCACGTCCGG GG ATG CGA AGT CTC AGC CTG GCG TGG CTG CTG GGA GGT            108
              Met Arg Ser Leu Ser Leu Ala Trp Leu Leu Gly Gly
               1               5                      10

ATC ACC CTT CTG GCG GCC TCG GTC TCC TGC AGC CGG ACC GAG AAC CTT          156
Ile Thr Leu Leu Ala Ala Ser Val Ser Cys Ser Arg Thr Glu Asn Leu
             15                  20                  25

GCA CCG GGA CGC AAC AAC AGT AAA GGA AGA AGT CTT ATT GGC AGA TTA          204
Ala Pro Gly Arg Asn Asn Ser Lys Gly Arg Ser Leu Ile Gly Arg Leu
         30                  35                  40

GAA ACC CAG CCT CCA ATC ACT GGG AAA GGG GTT CCG GTA GAA CCA GGC          252
Glu Thr Gln Pro Pro Ile Thr Gly Lys Gly Val Pro Val Glu Pro Gly
 45                  50                  55                  60

TTT TCC ATC GAT GAG TTC TCT GCG TCC ATC CTC ACC GGG AAG CTG ACC          300
Phe Ser Ile Asp Glu Phe Ser Ala Ser Ile Leu Thr Gly Lys Leu Thr
                 65                  70                  75

ACG GTC TTT CTT CCG GTC GTC TAC ATT ATT GTG TTT GTG ATT GGT TTG          348
Thr Val Phe Leu Pro Val Val Tyr Ile Ile Val Phe Val Ile Gly Leu
             80                  85                  90

CCC AGT AAT GGC ATG GCC CTC TGG ATC TTC CTT TTC CGA ACG AAG AAG          396
Pro Ser Asn Gly Met Ala Leu Trp Ile Phe Leu Phe Arg Thr Lys Lys
         95                 100                 105

AAA CAC CCC GCC GTG ATT TAC ATG GCC AAC CTG GCC TTG GCC GAC CTC          444
Lys His Pro Ala Val Ile Tyr Met Ala Asn Leu Ala Leu Ala Asp Leu
110                 115                 120

CTC TCT GTC ATC TGG TTC CCC CTG AAG ATC TCC TAC CAC CTA CAT GGC          492
Leu Ser Val Ile Trp Phe Pro Leu Lys Ile Ser Tyr His Leu His Gly
125                 130                 135                 140

AAC AAC TGG GTC TAC GGG GAG GCC CTG TGC AAG GTG CTC ATT GGC TTT          540
Asn Asn Trp Val Tyr Gly Glu Ala Leu Cys Lys Val Leu Ile Gly Phe
                145                 150                 155

TTC TAT GGT AAC ATG TAT TGC TCC ATC CTC TTC ATG ACC TGC CTC AGC          588
Phe Tyr Gly Asn Met Tyr Cys Ser Ile Leu Phe Met Thr Cys Leu Ser
            160                 165                 170

GTG CAG AGG TAC TGG GTG ATC GTG AAC CCC ATG GGA CAC CCC AGG AAG          636
Val Gln Arg Tyr Trp Val Ile Val Asn Pro Met Gly His Pro Arg Lys
```

-continued

|  |  |  | 175 |  |  |  | 180 |  |  |  | 185 |  |  |  |  |
|---|---|---|---|---|---|---|---|---|---|---|---|---|---|---|---|
| AAG | GCA | AAC | ATC | GCC | GTT | GGC | GTC | TCC | TTG | GCA | ATC | TGG | CTC | CTG | ATT | 684
| Lys | Ala | Asn | Ile | Ala | Val | Gly | Val | Ser | Leu | Ala | Ile | Trp | Leu | Leu | Ile |
| 190 |  |  |  |  | 195 |  |  |  |  | 200 |  |  |  |  |  |
| TTT | CTG | GTC | ACC | ATC | CCT | TTG | TAT | GTC | ATG | AAG | CAG | ACC | ATC | TAC | ATT | 732
| Phe | Leu | Val | Thr | Ile | Pro | Leu | Tyr | Val | Met | Lys | Gln | Thr | Ile | Tyr | Ile |
| 205 |  |  |  |  | 210 |  |  |  |  | 215 |  |  |  |  | 220 |
| CCA | GCA | TTG | AAC | ATC | ACC | ACC | TGT | CAC | GAT | GTG | CTG | CCT | GAG | GAG | GTA | 780
| Pro | Ala | Leu | Asn | Ile | Thr | Thr | Cys | His | Asp | Val | Leu | Pro | Glu | Glu | Val |
|  |  |  |  | 225 |  |  |  |  | 230 |  |  |  |  | 235 |  |
| TTG | GTG | GGG | GAC | ATG | TTC | AAT | TAC | TTC | CTC | TCA | CTG | GCC | ATT | GGA | GTC | 828
| Leu | Val | Gly | Asp | Met | Phe | Asn | Tyr | Phe | Leu | Ser | Leu | Ala | Ile | Gly | Val |
|  |  |  | 240 |  |  |  |  | 245 |  |  |  |  | 250 |  |  |
| TTC | CTG | TTC | CCG | GCC | CTC | CTT | ACT | GCA | TCT | GCC | TAC | GTG | CTC | ATG | ATC | 876
| Phe | Leu | Phe | Pro | Ala | Leu | Leu | Thr | Ala | Ser | Ala | Tyr | Val | Leu | Met | Ile |
|  |  | 255 |  |  |  |  | 260 |  |  |  |  | 265 |  |  |  |
| AAG | ACG | CTC | CGC | TCT | TCT | GCT | ATG | GAT | GAA | CAC | TCA | GAG | AAG | AAA | AGG | 924
| Lys | Thr | Leu | Arg | Ser | Ser | Ala | Met | Asp | Glu | His | Ser | Glu | Lys | Lys | Arg |
| 270 |  |  |  |  | 275 |  |  |  |  | 280 |  |  |  |  |  |
| CAG | AGG | GCT | ATC | CGA | CTC | ATC | ATC | ACC | GTG | CTG | GCC | ATG | TAC | TTC | ATC | 972
| Gln | Arg | Ala | Ile | Arg | Leu | Ile | Ile | Thr | Val | Leu | Ala | Met | Tyr | Phe | Ile |
| 285 |  |  |  |  | 290 |  |  |  |  | 295 |  |  |  |  | 300 |
| TGC | TTT | GCT | CCT | AGC | AAC | CTT | CTG | CTC | GTA | GTG | CAT | TAT | TTC | CTA | ATC | 1020
| Cys | Phe | Ala | Pro | Ser | Asn | Leu | Leu | Leu | Val | Val | His | Tyr | Phe | Leu | Ile |
|  |  |  |  | 305 |  |  |  |  | 310 |  |  |  |  | 315 |  |
| AAA | ACC | CAG | AGG | CAG | AGC | CAC | GTC | TAC | GCC | CTC | TAC | CTT | GTC | GCC | CTC | 1068
| Lys | Thr | Gln | Arg | Gln | Ser | His | Val | Tyr | Ala | Leu | Tyr | Leu | Val | Ala | Leu |
|  |  |  | 320 |  |  |  |  | 325 |  |  |  |  | 330 |  |  |
| TGC | CTG | TCG | ACC | CTC | AAC | AGC | TGC | ATA | GAC | CCC | TTT | GTC | TAT | TAC | TTT | 1116
| Cys | Leu | Ser | Thr | Leu | Asn | Ser | Cys | Ile | Asp | Pro | Phe | Val | Tyr | Tyr | Phe |
|  |  | 335 |  |  |  |  | 340 |  |  |  |  | 345 |  |  |  |
| GTC | TCA | AAA | GAT | TTC | AGG | GAT | CAC | GCC | AGA | AAC | GCG | CTC | CTC | TGC | CGA | 1164
| Val | Ser | Lys | Asp | Phe | Arg | Asp | His | Ala | Arg | Asn | Ala | Leu | Leu | Cys | Arg |
|  | 350 |  |  |  |  | 355 |  |  |  |  | 360 |  |  |  |  |
| AGT | GTC | CGC | ACT | GTG | AAT | CGC | ATG | CAA | ATC | TCG | CTC | AGC | TCC | AAC | AAG | 1212
| Ser | Val | Arg | Thr | Val | Asn | Arg | Met | Gln | Ile | Ser | Leu | Ser | Ser | Asn | Lys |
| 365 |  |  |  |  | 370 |  |  |  |  | 375 |  |  |  |  | 380 |
| TTC | TCC | AGG | AAG | TCC | GGC | TCC | TAC | TCT | TCA | AGC | TCA | ACC | AGT | GTT | AAA | 1260
| Phe | Ser | Arg | Lys | Ser | Gly | Ser | Tyr | Ser | Ser | Ser | Thr | Ser | Val | Lys |  |
|  |  |  |  | 385 |  |  |  |  | 390 |  |  |  |  | 395 |  |

ACC TCC TAC TGAGCTGTAC CTGAGGATGT CAAGCCTGCT TGATGATGAT       1309
Thr Ser Tyr

GATGATGATG GTGTGTGTGT GTGTGTGTGT GTGTGTGTGT GTGTGTGTGT GCACCCGTGT       1369

GTGAGTGCGT GGTAGGGATA CACCAACATG GATGGGGCTG TCATTTCCTA TCCAAGCTGT       1429

CTGTCTCTGC ACCAATCACA AGCATGCAGC TCTCCCCAGG ATTGACAGAA GCCTCCTCCT       1489

TTGCATGAGA ACAGTCTTCC ACTCTGATGA AAAGCATCAG TATCAGAAAC TGAAACGAAC       1549

TGAGAGGAGC TTGTTTTGTG AAAGTGAAGA GAAGATGGAG GGTCAGTGAC TTGCAAAAAA       1609

AACCAACCAA ACAAAAACTA CACCTGGCAA GAAGGCTAAG ACTCTCTGAA ATGCTTCCCT       1669

TTTCCATCTG GAGTTCGTCT CGGCCTTGTT CAGGACCTGA GGCCCTGGTA GAGCTTCAGT       1729

CCAGTTGATT GACTTTACAG ACTTGAGAGA GGAGTGAATG AGGAGTGAAT GAGGCTCCTG       1789

GCGGCATCCT AACCGGCTAA CAGTGGCCTT GCTGGACAAT AGGATTCAGA TGGCTGGAGT       1849

TACATTCTCA CACCATTTCA TCAGAACTAT TGGGGATCTT GATCAATGTG CAGGTCCCTT       1909

AGCGTCAGTA ACCCTGGGAG CTCAGACACG ATGGGGGTGA GGGTGGGGGT GGGGGTGGGG       1969

GTGAGGCTCT ACAAACCTTA GTGATGACTG CAGACACAGA ACCATGGAGC TGAGCCTGCT       2029

| | | | | | |
|---|---|---|---|---|---|
| TCTGCTTGCC | AGGGCACCAC | TGTAATGTTG | GCAAAGAAAA | ACCAACAGCA | GTGTTTTGAG | 2089
| CCTCTTTTTT | TGGTCAGTTT | ATGATGAATT | TGCCTATTGG | TTATTGGGA | TTTTCAGTTC | 2149
| CTTTATTACT | TTGTTGTAAT | TTGTGTGTT | TATTAGTCAA | GAAAAGAAG | ATGAGGCTCT | 2209
| TAAAAATGTA | AATAAAATTT | TTGGTTTTTT | GGTTTTTAA | CTTGGGCCAA | CTACAAATAC | 2269
| TGCTTAGGTT | TTTTTCTAAC | TTAATTGTTA | ACTACATCAT | GTGAACTTAA | GACATTTTCA | 2329
| TGATAAAGCA | TTACTGTAGT | GTCAGTTTTC | CCTCATCCTC | GATCATAGTC | CTTCCCGTGA | 2389
| AGCAGGGCCC | TTCCCCTCCC | CCCCCTTTGC | CGTTTCCCTC | CCACCAGAT | AGTCCCCTG | 2449
| TCTGCTTTAA | CCTACCAGTT | AGTATTTAT | AAAAACAGAT | CATTGGAATA | TTTATTATCA | 2509
| GTTTGTTCA | CTTGTTATCA | GTTTGTTCA | CTAATTGTC | CAATAATGGA | ATTAACGTCT | 2569
| TCTCATCTGT | TTGAGGAAGA | TCTGAAACAA | GGGGCCATTG | CAGGAGTACA | TGGCTCCAGG | 2629
| CTTACTTTAT | ATACTGCCTG | TATTTGTGGC | TTTAAAAAAA | TGACCTTGTT | ATATGAATGC | 2689
| TTTATAAATA | AATAATGCAT | GAACTTTAAA | AAAAAAAAA | AAA | | 2732

(2) INFORMATION FOR SEQ ID NO:61:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO:61:

```
Met Arg Ser Leu Ser Leu Ala Trp Leu Leu Gly Gly Ile Thr Leu Leu
 1               5                  10                  15

Ala Ala Ser Val Ser Cys Ser Arg Thr Glu Asn Leu Ala Pro Gly Arg
             20                  25                  30

Asn Asn Ser Lys Gly Arg Ser Leu Ile Gly Arg Leu Glu Thr Gln Pro
         35                  40                  45

Pro Ile Thr Gly Lys Gly Val Pro Val Glu Pro Gly Phe Ser Ile Asp
     50                  55                  60

Glu Phe Ser Ala Ser Ile Leu Thr Gly Lys Leu Thr Thr Val Phe Leu
 65                  70                  75                  80

Pro Val Val Tyr Ile Ile Val Phe Val Ile Gly Leu Pro Ser Asn Gly
                 85                  90                  95

Met Ala Leu Trp Ile Phe Leu Phe Arg Thr Lys Lys Lys His Pro Ala
            100                 105                 110

Val Ile Tyr Met Ala Asn Leu Ala Leu Ala Asp Leu Leu Ser Val Ile
        115                 120                 125

Trp Phe Pro Leu Lys Ile Ser Tyr His Leu His Gly Asn Asn Trp Val
    130                 135                 140

Tyr Gly Glu Ala Leu Cys Lys Val Leu Ile Gly Phe Phe Tyr Gly Asn
145                 150                 155                 160

Met Tyr Cys Ser Ile Leu Phe Met Thr Cys Leu Ser Val Gln Arg Tyr
                165                 170                 175

Trp Val Ile Val Asn Pro Met Gly His Pro Arg Lys Lys Ala Asn Ile
            180                 185                 190

Ala Val Gly Val Ser Leu Ala Ile Trp Leu Leu Ile Phe Leu Val Thr
        195                 200                 205

Ile Pro Leu Tyr Val Met Lys Gln Thr Ile Tyr Ile Pro Ala Leu Asn
    210                 215                 220

Ile Thr Thr Cys His Asp Val Leu Pro Glu Glu Val Leu Val Gly Asp
```

```
                225                     230                     235                     240
Met Phe Asn Tyr Phe Leu Ser Leu Ala Ile Gly Val Phe Leu Phe Pro
                245                     250                     255
Ala Leu Leu Thr Ala Ser Ala Tyr Val Leu Met Ile Lys Thr Leu Arg
                260                     265                     270
Ser Ser Ala Met Asp Glu His Ser Glu Lys Lys Arg Gln Arg Ala Ile
                275                     280                     285
Arg Leu Ile Ile Thr Val Leu Ala Met Tyr Phe Ile Cys Phe Ala Pro
                290                     295                     300
Ser Asn Leu Leu Leu Val Val His Tyr Phe Leu Ile Lys Thr Gln Arg
305                     310                     315                     320
Gln Ser His Val Tyr Ala Leu Tyr Leu Val Ala Leu Cys Leu Ser Thr
                325                     330                     335
Leu Asn Ser Cys Ile Asp Pro Phe Val Tyr Tyr Phe Val Ser Lys Asp
                340                     345                     350
Phe Arg Asp His Ala Arg Asn Ala Leu Leu Cys Arg Ser Val Arg Thr
                355                     360                     365
Val Asn Arg Met Gln Ile Ser Leu Ser Ser Asn Lys Phe Ser Arg Lys
                370                     375                     380
Ser Gly Ser Tyr Ser Ser Ser Ser Thr Ser Val Lys Thr Ser Tyr
385                     390                     395
```

(2) INFORMATION FOR SEQ ID NO:62:

(i) SEQUENCE CHARACTERISTICS:
    (A) LENGTH: 1414 base pairs
    (B) TYPE: nucleic acid
    (C) STRANDEDNESS: single
    (D) TOPOLOGY: linear (ix) FEATURE:
    (A) NAME/KEY: CDS
    (B) LOCATION: 50..1240

(ix) FEATURE:
    (A) NAME/KEY: mat_peptide
    (B) LOCATION: 50

(xi) SEQUENCE DESCRIPTION: SEQ ID NO:62:

```
CAAAGAATTG TAATACGACT CACTATAGGG CGAATTCGGA TCCAGGAGG ATG CGG      55
                                                       Met Arg
                                                       1

AGC CCC AGC GCG GCG TGG CTG CTG GGG GCC GCC ATC CTG CTA GCA GCC   103
Ser Pro Ser Ala Ala Trp Leu Leu Gly Ala Ala Ile Leu Leu Ala Ala
        5                   10                  15

TCT CTC TCC TGC AGT GGC ACC ATC CAA GGA ACC AAT AGA TCC TCT AAA   151
Ser Leu Ser Cys Ser Gly Thr Ile Gln Gly Thr Asn Arg Ser Ser Lys
 20                  25                  30

GGA AGA AGC CTT ATT GGT AAG GTT GAT GGC ACA TCC CAC GTC ACT GGA   199
Gly Arg Ser Leu Ile Gly Lys Val Asp Gly Thr Ser His Val Thr Gly
 35                  40                  45                  50

AAA GGA GTT ACA GTT GAA ACA GTC TTT TCT GTG GAT GAG TTT TCT GCA   247
Lys Gly Val Thr Val Glu Thr Val Phe Ser Val Asp Glu Phe Ser Ala
                 55                  60                  65

TCT GTC CTC GCT GGA AAA CTG ACC ACT GTC TTC CTT CCA ATT GTC TAC   295
Ser Val Leu Ala Gly Lys Leu Thr Thr Val Phe Leu Pro Ile Val Tyr
             70                  75                  80

ACA ATT GTG TTT GCG GTG GGT TTG CCA AGT AAC GGC ATG GCC CTA TGG   343
Thr Ile Val Phe Ala Val Gly Leu Pro Ser Asn Gly Met Ala Leu Trp
         85                  90                  95

GTC TTT CTT TTC CGA ACT AAG AAG AAG CAC CCT GCT GTG ATT TAC ATG   391
```

|     |     |     |     |     |     |     |     |     |     |     |     |     |     |     |     |
|-----|-----|-----|-----|-----|-----|-----|-----|-----|-----|-----|-----|-----|-----|-----|-----|
| Val | Phe | Leu | Phe | Arg | Thr | Lys | Lys | His | Pro | Ala | Val | Ile | Tyr | Met |     |
|     | 100 |     |     |     | 105 |     |     |     | 110 |     |     |     |     |     |     |

```
GCC  AAT  CTG  GCC  TTG  GCT  GAC  CTC  CTC  TCT  GTC  ATC  TGG  TTC  CCC  TTG       439
Ala  Asn  Leu  Ala  Leu  Ala  Asp  Leu  Leu  Ser  Val  Ile  Trp  Phe  Pro  Leu
115            120                 125                           130

AAG  ATT  GCC  TAT  CAC  ATA  CAT  GGC  AAC  AAC  TGG  ATT  TAT  GGG  GAA  GCT       487
Lys  Ile  Ala  Tyr  His  Ile  His  Gly  Asn  Asn  Trp  Ile  Tyr  Gly  Glu  Ala
                    135                 140                      145

CTT  TGT  AAT  GTG  CTT  ATT  GGC  TTT  TTC  TAT  CGC  AAC  ATG  TAC  TGT  TCC       535
Leu  Cys  Asn  Val  Leu  Ile  Gly  Phe  Phe  Tyr  Arg  Asn  Met  Tyr  Cys  Ser
               150                      155                      160

ATT  CTC  TTC  ATG  ACC  TGC  CTC  AGT  GTG  CAG  AGG  TAT  TGG  GTC  ATC  GTG       583
Ile  Leu  Phe  Met  Thr  Cys  Leu  Ser  Val  Gln  Arg  Tyr  Trp  Val  Ile  Val
          165                      170                      175

AAC  CCC  ATG  GGG  CAC  TCC  AGG  AAG  AAG  GCA  AAC  ATT  GCC  ATT  GGC  ATC       631
Asn  Pro  Met  Gly  His  Ser  Arg  Lys  Lys  Ala  Asn  Ile  Ala  Ile  Gly  Ile
          180                      185                      190

TCC  CTG  GCA  ATA  TGG  CTG  CTG  ACT  CTG  CTG  GTC  ACC  ATC  CCT  TTG  TAT       679
Ser  Leu  Ala  Ile  Trp  Leu  Leu  Thr  Leu  Leu  Val  Thr  Ile  Pro  Leu  Tyr
195                 200                      205                      210

GTC  GTG  AAG  CAG  ACC  ATC  TTC  ATT  CCT  GCC  CTG  AAC  ATC  ACG  ACC  TGT       727
Val  Val  Lys  Gln  Thr  Ile  Phe  Ile  Pro  Ala  Leu  Asn  Ile  Thr  Thr  Cys
                    215                      220                      225

CAT  GAT  GTT  TTG  CCT  GAG  CAG  CTC  TTG  GTG  GGA  GAC  ATG  TTC  AAT  TAC       775
His  Asp  Val  Leu  Pro  Glu  Gln  Leu  Leu  Val  Gly  Asp  Met  Phe  Asn  Tyr
               230                      235                      240

TTC  CTC  TCT  CTG  GCC  ATT  GGG  GTC  TTT  CTG  TTC  CCA  GCC  TTC  CTC  ACA       823
Phe  Leu  Ser  Leu  Ala  Ile  Gly  Val  Phe  Leu  Phe  Pro  Ala  Phe  Leu  Thr
          245                      250                      255

GCC  TCT  GCC  TAT  GTG  CTG  ATG  ATC  AGA  ATG  CTG  CGA  TCT  TCT  GCC  ATG       871
Ala  Ser  Ala  Tyr  Val  Leu  Met  Ile  Arg  Met  Leu  Arg  Ser  Ser  Ala  Met
260                 265                      270

GAT  GAA  AAC  TCA  GAG  AAG  AAA  AGG  AAG  AGG  GCC  ATC  AAA  CTC  ATT  GTC       919
Asp  Glu  Asn  Ser  Glu  Lys  Lys  Arg  Lys  Arg  Ala  Ile  Lys  Leu  Ile  Val
275                      280                      285                      290

ACT  GTC  CTG  GGC  ATG  TAC  CTG  ATC  TGC  TTC  ACT  CCT  AGT  AAC  CTT  CTG       967
Thr  Val  Leu  Gly  Met  Tyr  Leu  Ile  Cys  Phe  Thr  Pro  Ser  Asn  Leu  Leu
                    295                      300                      305

CTT  GTG  GTG  CAT  TAT  TTT  CTG  ATT  AAG  AGC  CAG  GGC  CAG  AGC  CAT  GTC      1015
Leu  Val  Val  His  Tyr  Phe  Leu  Ile  Lys  Ser  Gln  Gly  Gln  Ser  His  Val
               310                      315                      320

TAT  GCC  CTG  TAC  ATT  GTA  GCC  CTC  TGC  CTC  TCT  ACC  CTT  AAC  AGC  TGC      1063
Tyr  Ala  Leu  Tyr  Ile  Val  Ala  Leu  Cys  Leu  Ser  Thr  Leu  Asn  Ser  Cys
          325                      330                      335

ATC  GAC  CCC  TTT  GTC  TAT  TAC  TTT  GTT  TCA  CAT  GAT  TTC  AGG  GAT  CAT      1111
Ile  Asp  Pro  Phe  Val  Tyr  Tyr  Phe  Val  Ser  His  Asp  Phe  Arg  Asp  His
     340                      345                      350

GCA  AAG  AAC  GCT  CTC  CTT  TGC  CGA  AGT  GTC  CGC  ACT  GTA  AAG  CAG  ATG      1159
Ala  Lys  Asn  Ala  Leu  Leu  Cys  Arg  Ser  Val  Arg  Thr  Val  Lys  Gln  Met
355                      360                      365                      370

CAA  GTA  CCC  CTC  ACC  TCA  AAG  AAA  CAC  TCC  AGG  AAA  TCC  AGC  TCT  TAC      1207
Gln  Val  Pro  Leu  Thr  Ser  Lys  Lys  His  Ser  Arg  Lys  Ser  Ser  Ser  Tyr
               375                      380                      385

TCT  TCA  AGT  TCA  ACC  ACT  GTT  AAG  ACC  TCC  TAT  TGAGTTTTCC  AGGTCCTCAG      1260
Ser  Ser  Ser  Ser  Thr  Thr  Val  Lys  Thr  Ser  Tyr
               390                      395

ATGGGAATTG  CACAGTAGGA  TGTGGAACCT  GTTAATGTT  ATGAGGACGT  GTCTGTTATT           1320

TCCGGATCCA  GATCTTATTA  AAGCAGAACT  TGTTTATTGC  AGCTTATAAT  GGTTACAAAT           1380

AAAGCAATAG  CATCACAAAT  TTCACAAATA  AAGC                                         1414
```

( 2 ) INFORMATION FOR SEQ ID NO:63:

( i ) SEQUENCE CHARACTERISTICS:
        ( A ) LENGTH: 397 amino acids
        ( B ) TYPE: amino acid
        ( D ) TOPOLOGY: linear ( i i ) MOLECULE TYPE: protein ( x i ) SEQUENCE DESCRIPTION: SEQ ID NO:63:

```
Met Arg Ser Pro Ser Ala Ala Trp Leu Leu Gly Ala Ala Ile Leu Leu
 1               5                  10                  15
Ala Ala Ser Leu Ser Cys Ser Gly Thr Ile Gln Gly Thr Asn Arg Ser
             20                  25                  30
Ser Lys Gly Arg Ser Leu Ile Gly Lys Val Asp Gly Thr Ser His Val
         35                  40                  45
Thr Gly Lys Gly Val Thr Val Glu Thr Val Phe Ser Val Asp Glu Phe
     50                  55                  60
Ser Ala Ser Val Leu Ala Gly Lys Leu Thr Thr Val Phe Leu Pro Ile
65                  70                  75                  80
Val Tyr Thr Ile Val Phe Ala Val Gly Leu Pro Ser Asn Gly Met Ala
                 85                  90                  95
Leu Trp Val Phe Leu Phe Arg Thr Lys Lys Lys His Pro Ala Val Ile
                100                 105                 110
Tyr Met Ala Asn Leu Ala Leu Ala Asp Leu Leu Ser Val Ile Trp Phe
            115                 120                 125
Pro Leu Lys Ile Ala Tyr His Ile His Gly Asn Asn Trp Ile Tyr Gly
        130                 135                 140
Glu Ala Leu Cys Asn Val Leu Ile Gly Phe Phe Tyr Arg Asn Met Tyr
145                 150                 155                 160
Cys Ser Ile Leu Phe Met Thr Cys Leu Ser Val Gln Arg Tyr Trp Val
                165                 170                 175
Ile Val Asn Pro Met Gly His Ser Arg Lys Lys Ala Asn Ile Ala Ile
                180                 185                 190
Gly Ile Ser Leu Ala Ile Trp Leu Leu Thr Leu Leu Val Thr Ile Pro
            195                 200                 205
Leu Tyr Val Val Lys Gln Thr Ile Phe Ile Pro Ala Leu Asn Ile Thr
        210                 215                 220
Thr Cys His Asp Val Leu Pro Glu Gln Leu Leu Val Gly Asp Met Phe
225                 230                 235                 240
Asn Tyr Phe Leu Ser Leu Ala Ile Gly Val Phe Leu Phe Pro Ala Phe
                245                 250                 255
Leu Thr Ala Ser Ala Tyr Val Leu Met Ile Arg Met Leu Arg Ser Ser
            260                 265                 270
Ala Met Asp Glu Asn Ser Glu Lys Lys Arg Lys Arg Ala Ile Lys Leu
        275                 280                 285
Ile Val Thr Val Leu Gly Met Tyr Leu Ile Cys Phe Thr Pro Ser Asn
        290                 295                 300
Leu Leu Leu Val Val His Tyr Phe Leu Ile Lys Ser Gln Gly Gln Ser
305                 310                 315                 320
His Val Tyr Ala Leu Tyr Ile Val Ala Leu Cys Leu Ser Thr Leu Asn
                325                 330                 335
Ser Cys Ile Asp Pro Phe Val Tyr Tyr Phe Val Ser His Asp Phe Arg
                340                 345                 350
Asp His Ala Lys Asn Ala Leu Leu Cys Arg Ser Val Arg Thr Val Lys
```

|   | 355 |   |   |   |   | 360 |   |   |   |   | 365 |   |   |   |
|---|---|---|---|---|---|---|---|---|---|---|---|---|---|---|
| Gln | Met | Gln | Val | Pro | Leu | Thr | Ser | Lys | Lys | His | Ser | Arg | Lys | Ser | Ser |
|   | 370 |   |   |   |   | 375 |   |   |   |   | 380 |   |   |   |
| Ser | Tyr | Ser | Ser | Ser | Ser | Thr | Thr | Val | Lys | Thr | Ser | Tyr |
| 385 |   |   |   |   | 390 |   |   |   |   | 395 |   |   |